US010942170B2

(12) United States Patent
Tan et al.

(10) Patent No.: US 10,942,170 B2
(45) Date of Patent: Mar. 9, 2021

(54) QUANTITATIVE MEASUREMENT OF HUMAN BLASTOCYST AND MORULA MORPHOLOGY DEVELOPMENTAL KINETICS

(71) Applicant: Progyny, Inc., Menlo Park, CA (US)

(72) Inventors: Lei Tan, Menlo Park, CA (US); Martin Chian, Menlo Park, CA (US); Alice Chen Kim, Menlo Park, CA (US); Peter Lorenzen, Menlo Park, CA (US)

(73) Assignee: Ares Trading S.A., Aubonne (CH)

( * ) Notice: Subject to any disclaimer, the term of this patent is extended or adjusted under 35 U.S.C. 154(b) by 0 days.

(21) Appl. No.: 14/664,481

(22) Filed: Mar. 20, 2015

(65) Prior Publication Data
US 2015/0268227 A1 Sep. 24, 2015

Related U.S. Application Data

(60) Provisional application No. 61/968,260, filed on Mar. 20, 2014.

(51) Int. Cl.
C12N 5/00 (2006.01)
C12N 5/02 (2006.01)
G01N 33/50 (2006.01)
G01N 33/483 (2006.01)
G06T 7/00 (2017.01)
C12N 5/073 (2010.01)
G06K 9/00 (2006.01)
G01N 15/14 (2006.01)

(52) U.S. Cl.
CPC ....... G01N 33/5091 (2013.01); C12N 5/0604 (2013.01); G01N 15/1463 (2013.01); G01N 33/4833 (2013.01); G06K 9/00147 (2013.01); G06T 7/0016 (2013.01); G01N 2015/1493 (2013.01); G01N 2015/1497 (2013.01); G06T 2207/10056 (2013.01); G06T 2207/30044 (2013.01)

(58) Field of Classification Search
CPC ........... C12N 2517/10; G01N 33/5091; G01N 2015/1493; G01N 2015/1497; G06T 2207/3044
USPC ....................................................... 435/325
See application file for complete search history.

(56) References Cited

U.S. PATENT DOCUMENTS

| 6,757,423 | B1 | 6/2004 | Amini |
| 8,265,357 | B2 | 9/2012 | Ramsing et al. |
| 2010/0002929 | A1 | 1/2010 | Sammak |
| 2010/0055039 | A1 | 3/2010 | Doyonnas et al. |
| 2011/0092762 | A1 | 4/2011 | Wong |
| 2011/0105834 | A1 | 5/2011 | Wong et al. |
| 2011/0125719 | A1 | 5/2011 | Jayaraman |
| 2011/0207112 | A1 | 8/2011 | Burbank et al. |
| 2012/0244567 | A1 | 9/2012 | Zeng |
| 2014/0107991 | A1 | 4/2014 | Elashoff |

FOREIGN PATENT DOCUMENTS

| WO | 2007/144001 A2 | 12/2007 |
| WO | 2009/137866 A1 | 11/2009 |
| WO | 2012/047678 A2 | 4/2012 |
| WO | 2012/116185 A1 | 8/2012 |
| WO | 2012/163363 A1 | 12/2012 |
| WO | 2013/178785 A1 | 12/2013 |
| WO | 2014/121200 | 8/2014 |
| WO | 2014/121205 | 8/2014 |
| WO | 2014/134527 A1 | 9/2014 |
| WO | 2014/134550 A1 | 9/2014 |

OTHER PUBLICATIONS

Wong (2010, Nature Biotechnology, 18:1115-1121).*
Alfarawati et al., "Session 30: The Blastocyst," Human Reprod., (Jun. 2010), 25(S1):i41-i44. DOI:10.1093/humrepjde.25.s1.300-111.
Alikani, M., et al., "Noviable human pre-implantation embryos as a source of stem cells for research and potential therapy", Mol. Hum. Reprod., (2005): 11:335-344.
Campbell et al., "Modelling a risk classification of aneuploidy in human embryos using non-invasive morphokinetics," Reproductive Biomedicine Online, (Feb. 2013), 26(5):477-485.
Capalbo et al., "Correlation between standard blastocyst morphology. euploidy and implantation: an observational study in two centers involving 956 screened blastocysts,". Human Reprod., (Feb. 2014) 29(6):1173-1181.
De Kock et al, "0-121", Fertil. Steril., (2006), 86(3):S51-S52.
Dobson, T. et al., "The unique transcriptome through day 3 of human preimplantation development", Human Molecular Genetics, (2004): 13(14):1461-1470.
El-Toukhy et al., (2009) "A multi-centre randomised controlled study of pre-IVF outpatient hysteroscopy in women with recurrent IVF implantation failure: Trial of Outpatient Hysteroscopy— [TROPHY] in IVF," Reprod. Health, 6:20 (7 pages). doi: 10.1186/1742-4755-6-20. Epub Dec. 3, 2009.
Fenwick, et al., (2002) "Time from insemination to first cleavage predicts developmental competence of human preimplantation embryos in vitro," Human Reproduction, 17(2):407-412.
Filho et al, "A method for semi-automatic grading of human blastocyst microscope images," Human Reprod., (2012) 27(9):2641-2648.
Filho et al, "A review on automatic analysis of human embryo microscope images," The Open Biomedical Engineering Journal, (Jan. 2010), pp. 170-177, XP055192640, Netherlands, OOI: 10.2174/1874120701004010170, Retrieved from the Internet: www.ncbi.nlm.nih.govjpubmed/21379391.

(Continued)

Primary Examiner — Valarie E Bertoglio
(74) Attorney, Agent, or Firm — Medlen & Carroll, LLP

(57) ABSTRACT

Methods, compositions and kits for determining the developmental potential of one or more embryos are provided. These methods, compositions and kits find use in identifying embryos in vitro that are most useful in treating infertility in humans.

11 Claims, 15 Drawing Sheets

(56) References Cited

OTHER PUBLICATIONS

Fragouli, E. et al., "Comprehensive chromosome screening of polar bodies and blastocysts from couples experiencing repeated implantation failure," Fertil. Steril., 94(3):875-887 (2010) Epub Jun. 21, 2009.
Keltz MD, et al., (2006) "Predictors of embryo fragmentation and outcome after fragment removal in in vitro fertilization." Fertil Steril, 86:321-324.
Lundin, et al., (2001) "Early embryo cleavage is a strong indicator of embryo quality in human IVF," Human Reproduction, 16(12):2652-2657.
Magnusson et al. A batch algorithm using iterative application of the Viterbi algorithm to track 17, 18 cells and construct cell lineages. 2012 9th IEEE International Symposium on Biomedical Imaging (ISBI) May 5, 2012 pp. 382-385. [retrieved from http:l/ieeexplore.ieee.org/xpl/articleDetails.jsp?reload=true&arnumber-6235564 on May 2, 2014] Abstract.
Manipalviratn et al., "Imprinting disorders and assisted reproductive technology," Fertil Steril., Feb. 2009, 91(2):305-315.
Mastenbroek, S. et al., "In Vitro Fertilization with Preimplantation Genetic Screening," N. Engl. J. Med., 357(1):9-17 (2007).
Meng et al. Histology Image Classification Using Supervised Classification and 23 Multimodal Fusion. ISM '1 0 Proceedings of the 2010 IEEE International Symposium on Multimedia. 2010 pp. 145-152.
Milki, A. A. et al., "Accuracy of day 3 criteria for selecting the best embryos," Fertility and Sterility, 77(6):1191-1195 (2002).
Milki, A. A. et al., "Comparison of blastocyst transfer with day 3 embryo transfer in similar patient populations," Fertility and Sterility, 73(1):126-129 (2000).
Mtango, N. R., et al., "Oocyte quality and maternal control of development.", Int. Rev. Cell. Mol. Biol. 2008;268:223-290.
Nagy, Z. P. et al., "Time-course of oocyte activation, pronucleus formation and cleavage in human oocytes fertilized by intracytoplasmic sperm injection," Human Reproduction, 9(9):1743-1748 (1994).
Paternot et al., "Semi-automated morphometric analysis of human embryos can reveal correlations between total embryo volume and clinical pregnancy", Human Reprod., (2013), 28(3):627-633.
Payne, D. et al., "Preliminary observations on polar body extrusion and pronuclear formation in human oocytes using time-lapse video cinematography," Human Reproduction, 12(3):532-541 (1997).
Rienzi, L. et al., "Significance of morphological attributes of the early embryo.", Reprod. Biomed. Online May 2005; 10(5):669-681.
Rijinders, P. M. et al., "The predictive value of day 3 embryo morphology regarding blastocyst formation, pregnancy, and implantation rate after day 5 transfer following in vitro fertilization or intracytoplasmic sperm injection," Human Reproduction, 13(10):2869-2873 (1998).
Scotti. Automatic Morphological Analysis for Acute Leukemia Identification in Peripheral Blood Microscope Images. CIMSA 2005? IEEE International Conference on Computational Intelligence for Measurement Systems and Applications Jul. 2005 p. 96-101.
Sepúlveda, S. et al., "In vitro development and pregnancy outcomes for human embryos cultured in either a single medium or in a sequential media system", Fertil Steril. May 2009; 91(5):1765-70.
Swain, "Could time-lapse embryo imaging reduce the need for biopsy and PGS?" J. Assisted Reprod. Genet., (Jul. 2013), 30(8):1081-1090.
Taft, R. E., "Virtues and limitations of the preimplantation mouse embryo as a model system," Theriogenology, 69:10-16 (2008) Epub Nov. 19, 2007.
Vanneste, E. et al., "Chromosome instability is common in human cleavage-stage embryos," Nature Medicine, 15(5):577-583 (2009).
Wells D., et al.,"Comprehensive chromosomal analysis of human preimplantation embryos using whole genome amplification and single cell comparative genomic hydridization." Mol Hum Reprod, Nov. 2000;6(11):1055-62.
Yee et al., "An Automatic Model-Based Approach For Measuring The Zona Pellucida Thickness In Day Five Human Blastocysts," Proceedings Of The International Conference On Image Processing, Computer Vision, And Pattern Recognition (Ipcv), Jan. 1, 2013 (Jan. 1, 2013). p. 1. Xp055192636, Athens.
Zernicka-Goetz, M. "Patterning of the embryo: The first spatial decisions in the life of a mouse." Development Feb. 2002;129(4):815-829.
Zernicka-Goetz, M., "The first cell-fate decisions in the mouse embryo: destiny is a matter of both change and choice.", Curr. Opin. Genet. Dev., Aug. 2006;16(4):406-412.

\* cited by examiner

FIGURE 8
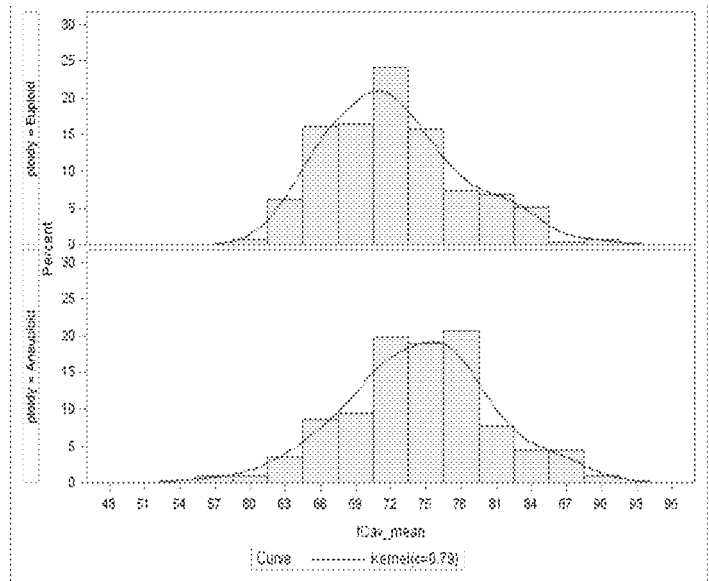
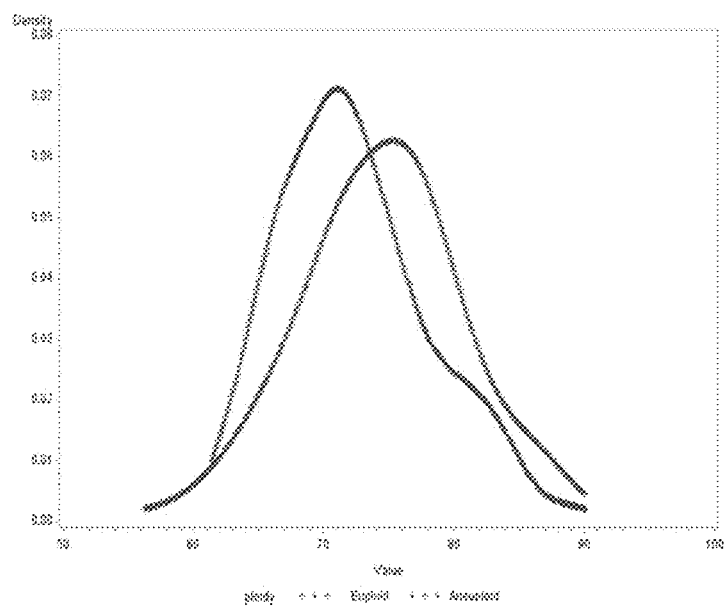
| Analysis Variable: tCav_mean | | | |
|---|---|---|---|
| Ploidy | N Obs | Mean | SD |
| Euploid | 278 | 72.28 | 5.72 |
| Aneuploid | 128 | 74.40 | 6.22 |

FIGURE 11
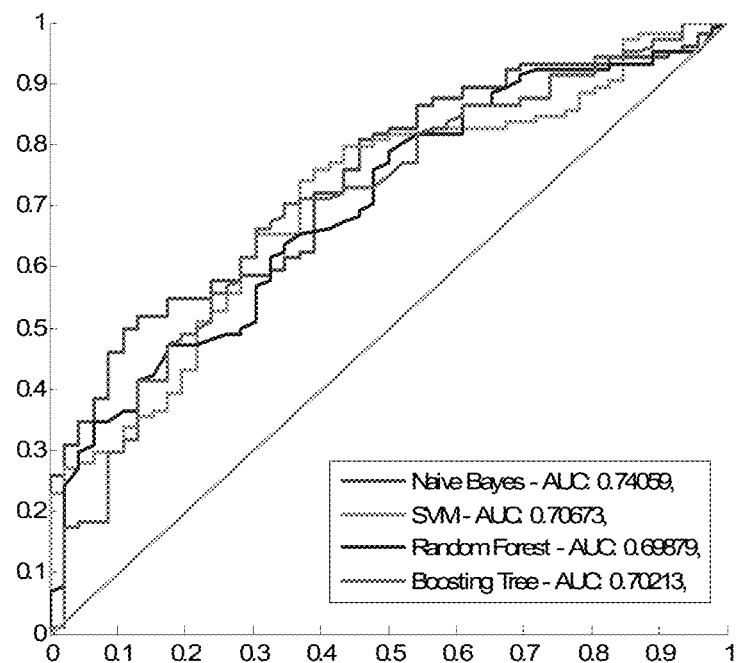
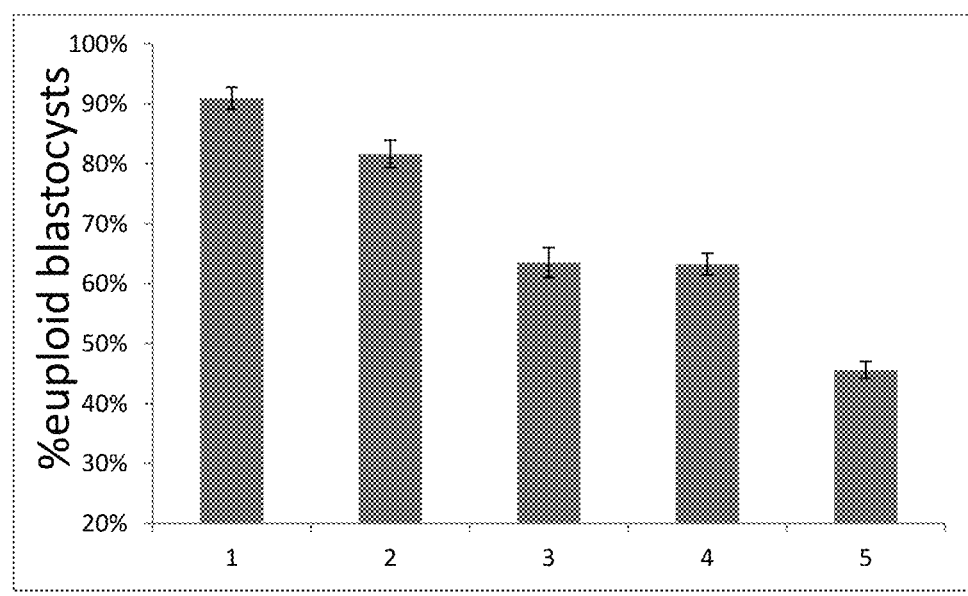

QUANTITATIVE MEASUREMENT OF HUMAN BLASTOCYST AND MORULA MORPHOLOGY DEVELOPMENTAL KINETICS

CROSS REFERENT TO RELATED APPLICATIONS

This application claims priority to U.S. Provisional Patent Application No. 61/968,260 filed Mar. 20, 2014, the contents of which are incorporated by reference herein in its entirety.

FIELD OF THE INVENTION

This invention relates to the field of biological and clinical testing, and particularly the imaging and evaluation of zygotes/embryos from both humans and animals.

BACKGROUND OF THE INVENTION

Infertility is a common health problem that affects 10-15% of couples of reproductive-age. In the United States alone in the year 2006, approximately 140,000 cycles of in vitro fertilization (IVF) were performed (cdc.gov/art). This resulted in the culture of more than a million embryos annually with variable, and often ill-defined, potential for implantation and development to term. The live birth rate, per cycle, following IVF was just 29%, while on average 30% of live births resulted in multiple gestations (cdc.gov/art). Multiple gestations have well-documented adverse outcomes for both the mother and fetuses, such as miscarriage, pre-term birth, and low birth rate. Potential causes for failure of IVF are diverse; however, since the introduction of IVF in 1978, one of the major challenges has been to identify the embryos that are most suitable for transfer and most likely to result in term pregnancy.

The understanding in the art of basic embryo development is limited as studies on human embryo biology remain challenging and often exempt from research funding. Consequently, most of the current knowledge of embryo development derives from studies of model organisms. Embryos from different species go through similar developmental stages, however, the timing varies by species. These differences and many others make it inappropriate to directly extrapolate from one species to another. (Taft, R. E. (2008) Theriogenology 69(1):10-16). The general pathways of human development, as well as the fundamental underlying molecular determinants, are unique to human embryo development. For example, in mice, embryonic transcription is activated approximately 12 hours post-fertilization, concurrent with the first cleavage division, whereas in humans embryonic gene activation (EGA) occurs on day 3, around the 8-cell stage (Bell, C. E., et al. (2008) Mol. Hum. Reprod. 14:691-701; Braude, P., et al. (1988) Nature 332:459-461; Hamatani, T. et al. (2004) Proc. Natl. Acad. Sci. 101:10326-10331; Dobson, T. et al. (2004) Human Molecular Genetics 13(14):1461-1470). In addition, the genes that are modulated in early human development are unique (Dobson, T. et al. (2004) Human Molecular Genetics 13(14):1461-1470). Moreover, in other species such as the mouse, more than 85% of embryos cultured in vitro reach the blastocyst stage, one of the first major landmarks in mammalian development, whereas cultured human embryos have an average blastocyst formation rate of approximately 30-50%, with a high incidence of mosaicism and aberrant phenotypes, such as fragmentation and developmental arrest (Rienzi, L. et al. (2005) Reprod. Biomed. Online 10:669-681; Alikani, M., et al. (2005) Mol. Hum. Reprod. 11:335-344; Keltz, M. D., et al. (2006) Fertil. Steril. 86:321-324; French, D. B., et al. (2009) Fertil. Steril.). In spite of such differences, the majority of studies of preimplantation embryo development derive from model organisms and are difficult to relate to human embryo development (Zernicka-Goetz, M. (2002) Development 129:815-829; Wang, Q., et al. (2004) Dev Cell. 6:133-144; Bell, C. E., et al. (2008) Mol. Hum. Reprod. 14:691-701; Zernicka-Goetz, M. (2006) Curr. Opin. Genet. Dev. 16:406-412; Mtango, N. R., et al. (2008) Int. Rev. Cell. Mol. Biol. 268:223-290).

Traditionally in IVF clinics, human embryo viability has been assessed by simple morphologic observations such as the presence of uniformly-sized, mononucleate blastomeres and the degree of cellular fragmentation (Rijinders P M, Jansen C A M. (1998) Hum Reprod 13:2869-73; Milki A A, et al. (2002) Fertil Steril 77:1191-5). More recently, additional methods such as extended culture of embryos (to the blastocyst stage at day 5) and analysis of chromosomal status via preimplantation genetic diagnosis (PGD) have also been used to assess embryo quality (Milki A, et al. (2000) Fertil Steril 73:126-9; Fragouli E, (2009) Fertil Steril Jun 21 [EPub ahead of print]; El-Toukhy T, et al. (2009) Hum Reprod 6:20; Vanneste E, et al. (2009) Nat Med 15:577-83). However, potential risks of these methods also exist in that they prolong the culture period and disrupt embryo integrity (Manipalviratn S, et al. (2009) Fertil Steril 91:305-15; Mastenbroek S, et al. (2007) N Engl J Med. 357:9-17).

Single-embryo transfer (SET) is currently the preferred practice in in vitro fertilization (IVF) treatment in order to reduce the risk for adverse outcomes associated with multiple gestation pregnancy. For SET, embryologists need a reliable embryo selection method that allows for consistent identification of embryos with the highest developmental potential. Recently, time-lapse analysis of embryo development kinetics has been shown to provide valuable information to improve embryo selection and subsequent pregnancy outcomes. Filho et al. (Hum. Reprod. (2012) 27(9):2641-2648) describe a method of morphologically grading blastocyst trophectoderm and inner cell mass using static microscope images. Studies by Iwata et al. (Hum. Reprod. (2010) 25(Suppl. 1):141-144), Campbell et al. (Reproductive Bio-Medicine Online, 9 May 2013), and Mazur et al. (Hum. Reprod. (2013) 28(Suppl. 1):1149-1206) describe correlations between human embryo quality and timings of compaction, cavitation, expansion and/or collapse using manual video analysis.

However, manual review of time-lapse videos is labor-intensive and time-consuming. Furthermore, manual assessment is subject to high inter- and intra-observer variations. This is especially problematic for time-lapse parameters that involve morula and/or blastocyst stage events (e.g., compaction, cavitation, expansion and collapse), as these events occur in a gradual fashion, and it is difficult for human observers to mark each event beginning and end points in a consistent and reproducible manner.

Not withstanding the recent developments in time lapse imaging that allow clinicians to select embryos with greater developmental potential based on timing parameters of the first few cell cycles, current embryo selection relies primarily on morphological evaluations which are very subjective and offer limited predictive value of embryo viability. Failure to correctly identify the most viable embryos can lead to unsuccessful IVF treatment or multiple gestation pregnancy. Time-lapse imaging technology allows real time embryo monitoring and provides additional insight into human embryo developmental biology. This technology has allowed for the identification and measurement of new morphological and timing parameters that may impact embryo development including the morula and/or blastocyst stage events as described herein.

SUMMARY OF THE INVENTION

The invention provides for quantitative assessment of dynamic changes of human embryo morphology at the morula and/or blastocyst stage using imaging features. In particular, methods for measuring compaction, cavitation and blastocyst expansion and collapse kinetics are provided. These methods are useful in methods of treating infertility in humans and other animals.

One aspect of the invention provides methods for determining the duration of compaction and/or cavitation and/or expansion and/or collapse. In one embodiment, a method for measuring the duration of compaction, cavitation, expansion and/or collapse comprises the steps of culturing one or more embryos under conditions sufficient for embryo development; time lapse imaging said one or more embryos; and analyzing one or more image features, thereby determining (1) an onset of compaction, cavitation, expansion or collapse and (2) a resolution of compaction, cavitation, expansion and/or collapse. In one embodiment, the duration of blastocyst expansion and collapse is determined. In a further embodiment, the one or more image feature is an area defined by an embryo outer boundary, texture at the area around the embryo edge, texture at the embryo center, local image feature detectors such as edges, corners/interest points, blobs (regions of interest), and ridges. In another embodiment, the method further comprises measuring one or more cellular parameters selected from the duration of expansion; the duration of collapse; the time interval between expansion and collapse, the frequency of collapse, the rate of expansion; the rate of collapse, average embryo size after initial expansion, the degree of expansion, and the degree of collapse In one embodiment, the method comprises measuring one or more cellular parameters in a single plane (i.e. 2 dimensional). In another embodiment, the method comprises measuring the one or more cellular parameters in multiple planes (i.e. 3 dimensional). In one embodiment, the imaging employs darkfield illumination, brightfield illumination or combination of these two modalities. In one embodiment, the method comprises measuring one or more cellular parameters and/or image features selected from the time interval between beginning or end of a cytokinesis or cell cycle event to the onset or resolution of compaction, cavitation, expansion or collapse. In one embodiment, the method comprises measuring the time interval between the beginning or end of cytokinesis 1 to the onset or resolution of compaction, cavitation, expansion or collapse. In another embodiment, the method comprises measuring the time interval between the beginning or end of cytokinesis 2 to the onset or resolution of compaction, cavitation, expansion or collapse. In another embodiment, the method comprises measuring the time interval between the beginning or end of cytokinesis 3 to the onset or resolution of compaction, cavitation, expansion or collapse. In another embodiment, the method comprises measuring the time interval between the beginning or end of cytokinesis 4 to the onset or resolution of compaction, cavitation, expansion or collapse. In another embodiment, the method comprises measuring the time interval between the beginning or end of cytokinesis 5 to the onset or resolution of compaction, cavitation, expansion or collapse. In another embodiment, the method comprises measuring the time interval between the beginning or end of cell cycle 1 to the onset or resolution of compaction, cavitation, expansion or collapse. In another embodiment, the method comprises measuring the time interval between the beginning or end of cell cycle 2 to the onset or resolution of compaction, cavitation, expansion or collapse. In another embodiment, the method comprises measuring the time interval between the beginning or end of cell cycle 3 to the onset or resolution of compaction, cavitation, expansion or collapse. In another embodiment, the method comprises measuring the time interval between the beginning or end of cell cycle 4 to the onset or resolution of compaction, cavitation, expansion or collapse. In another embodiment, the method comprises measuring the time interval between the beginning or end of cell cycle 5 to the onset or resolution of compaction, cavitation, expansion or collapse.

In one embodiment, the duration of compaction is determined. In a further embodiment, the one or more image feature is spatial distribution of the cell boundary segments, average intensity over a region around embryo center, or standard deviation of intensity at embryo center. In another embodiment, the method further comprises measuring one or more cellular parameters selected from embryo shape; texture at the area around the embryo edge; texture at embryo center; local image feature detectors such as edges, corners/interest points, blobs (regions of interest), ridges. Feature extraction and description methods such as Canny, Sobel, scale invariant feature transform (SIFT); speeded up robust features (SURF); can all be used. These features can then be utilized in measuring multiple embryo developmental events and subsequent time intervals between events, such as time interval between compaction and cavitation.

In one embodiment, the duration of cavitation is determined. In a further embodiment, the one or more image feature is cell boundary segment distribution, average intensity at embryo center, or standard deviation of intensity at embryo center. In another embodiment, the method further comprises measuring one or more cellular parameters selected from embryo shape; texture at embryo edge; texture at embryo center; global or local image features such as key point descriptors that may include or be based on scale invariant feature transform (SIFT), speeded up robust features (SURF), or other suitable descriptors known to one of skill in the art including Local Binary Patterns (LBP), SIFT-like GLOH features, PCA-SIFT, SIFT-Rank descriptor; and a time interval between compaction and cavitation.

In certain embodiments, the one or more embryos are produced by fertilization of oocytes in vitro. In a further embodiment, the oocytes are matured in vitro. In yet a further embodiment, the oocytes matured in vitro are supplemented with growth factors. In another embodiment, the one or more embryos have not been frozen prior to culturing. In yet another embodiment, the one or more embryos have been frozen prior to culturing.

In one embodiment, the measuring step is automated. In another embodiment, the imaging acquires images that are digitally stored. In one embodiment, the imaging employs darkfield illumination, brightfield illumination, or a combination of the two imaging modalities. Other modalities can also be used such as phase contrast, Hoffman modulation contrast, differential interference contrast, polarized light, fluorescence, single or multiplane or combinations thereof. In some embodiments, darkfield illumination may be used to provide enhanced image contrast for subsequent feature extraction and image analysis.

In one embodiment, the one or more human embryos are placed in a culture dish prior to culturing under conditions sufficient for embryo development. In a further embodiment, the culture dish comprises a plurality of microwells. In another embodiment, one or more human embryos is placed within a microwell prior to culturing under conditions sufficient for embryo development. In one embodiment, the measuring is carried out at an imaging station.

One aspect of the invention provides methods for determining the likelihood that one or more embryos is/are euploid, will reach the blastocyst stage, become a good quality blastocyst, implant into the uterus and/or be born live. In some aspects determining the likelihood of euploidy and/or reaching the blastocyst stage and/or becoming a good quality blastocyst and/or implanting into the uterus is determined by deselecting with high specificity one or more human embryos that is likely to be aneuploid, not likely to reach the blastocyst stage, become a good quality blastocyst, implant into the uterus or be born live. In such aspects, time-lapse imaging parameters such as compaction and/or cavitation and/or expansion and/or collapse parameters of an embryo are measured to arrive at a parameter measurement which are be employed to provide a determination of the likelihood of the embryo to be euploid, reach the blastocyst stage, become a good quality blastocyst, implant into a uterus, and/or be born live which determination may be used to guide a clinical course of action. In some embodiments, clinical variables such as patient age, number of eggs retrieved and fertilization rate are used together with time-lapse imaging parameters such as compaction and/or cavitation and/or expansion and/or collapse parameters of an embryo are measured to arrive at a parameter measurement which are be employed to provide a determination of the likelihood of the embryo to be euploid, reach the blastocyst stage, become a good quality blastocyst, implant into a uterus, and/or be born live. In some embodiments, the compaction and/or cavitation and/or expansion and/or collapse parameter is a morphological event that is measurable by time-lapse microscopy. In one embodiment, the method comprises determining the likelihood of the embryo being euploid or aneuploid by measuring one or more cellular parameters and/or image features selected from the time interval between beginning or end of a cytokinesis or cell cycle event to the onset or resolution of compaction, cavitation, expansion or collapse. In one embodiment, the method comprises measuring the time interval between the beginning or end of cytokinesis 1 to the onset or resolution of compaction, cavitation, expansion or collapse. In another embodiment, the method comprises measuring the time interval between the beginning or end of cytokinesis 2 to the onset or resolution of compaction, cavitation, expansion or collapse. In another embodiment, the method comprises measuring the time interval between the beginning or end of cytokinesis 3 to the onset or resolution of compaction, cavitation, expansion or collapse. In another embodiment, the method comprises measuring the time interval between the beginning or end of cytokinesis 4 to the onset or resolution of compaction, cavitation, expansion or collapse. In another embodiment, the method comprises measuring the time interval between the beginning or end of cytokinesis 5 to the onset or resolution of compaction, cavitation, expansion or collapse. In another embodiment, the method comprises measuring the time interval between the beginning or end of cell cycle 1 to the onset or resolution of compaction, cavitation, expansion or collapse. In another embodiment, the method comprises measuring the time interval between the beginning or end of cell cycle 2 to the onset or resolution of compaction, cavitation, expansion or collapse. In another embodiment, the method comprises measuring the time interval between the beginning or end of cell cycle 3 to the onset or resolution of compaction, cavitation, expansion or collapse. In another embodiment, the method comprises measuring the time interval between the beginning or end of cell cycle 4 to the onset or resolution of compaction, cavitation, expansion or collapse. In another embodiment, the method comprises measuring the time interval between the beginning or end of cell cycle 5 to the onset or resolution of compaction, cavitation, expansion or collapse.

In one embodiment, the invention provides methods for determining the likelihood that an embryo will be aneuploid. In one embodiment, the invention provides for methods of distinguishing between types of aneuploidy. In one embodiment, the invention provides for methods of determining the likelihood that an embryo will display a complex aneuploidy. In one embodiment, the complex aneuploidy is an aneuploidy of 2 or more chromosomes. In another embodiment, the complex aneuploidy is an aneuploidy of 3 or more chromosomes. In another embodiment, the complex aneuploidy is an aneuploidy of 4 or more chromosomes. In another embodiment, the complex aneuploidy is an aneuploidy of 5 or more chromosomes. In another embodiment, the complex aneuploidy is an aneuploidy of more than 6 chromosomes. In another embodiment, the invention provides for methods of determining the likelihood that an embryo will have a non-viable aneuploidy. In one embodiment the non-viable aneuploidy is trisomy 2. In another embodiment, the non-viable aneuploidy is monosomy 1. In yet another embodiment, the non-viable aneuploidy is both trisomy 2 and monosomy 1. In still another embodiment, the non-viable aneuploidy is a complex aneuploidy comprising as one of its 2 or more aneuploid chromosomes, trisomy 2 or monosomy 1. In still a further embodiment, the invention provides for methods of determining the likelihood that an embryo has a disease causing aneuploidy which may be either a viable or non-viable aneuploidy. In one embodiment, the disease causing aneuploidy is trisomy 21, trisomy 18, trisomy 13, trisomy 16, trisomy 22 or sex chromosome aneuploidies such as monosomy X or XXY.

In one embodiment, chromosomal content (i.e. euploid vs. aneuploid) in embryos is assessed/can be confirmed by qPCR-based comprehensive chromosomal screening (Treff and Scott, (2013) Fertil. Steril. 99(4):1049-53). In another embodiment, chromosomal content is assessed/can be confirmed by array-based Comparative Genomic Hybridization (aCGH, Wells and Delhanty, (2000) 6(11):1055-62). In yet another embodiment, chromosomal content is Assessed/can be confirmed by karyomapping (Handyside et al, (2010) J. Med. Genet. 47(10):651-8). In yet another embodiment, chromosomal content is assessed/can be confirmed by Single Nucleotide Polymorphism (SNP) array (van Uum et al, (2012) Eur. J. Genet. 20(9):938-44). In Another embodiment, chromosomal content is assessed/can be confirmed by Next-Generation Sequencing (NGS, Treff et al (2013) Fertil. Steril. 100:S82).

One aspect of the invention provides methods for ranking the likelihood of an embryo or blastocyst being euploid within a patient's available embryos or blastocysts, so that the probability of selecting a euploid embryo for transfer is maximized, and time to pregnancy is minimized. In some aspects of the invention, methods are provided for ranking the likelihood that an embryo is euploid, or will become a euploid blastocyst. In such aspects, compaction and/or cavitation and/or expansion and/or collapse parameters of an embryo are measured to arrive at a parameter measurement which can be employed to provide ranking of the likelihood of the embryo to be euploid or become a euploid blastocyst, thereby providing a means for selecting the embryo with highest likelihood being euploid for transfer. In some embodiments, the compaction and/or cavitation and/or expansion and/or collapse parameter is a morphological event that is measurable by time-lapse microscopy.

One aspect of the invention provides methods for determining the likelihood that one or more euploid embryos will implant into the uterus or be born live. In such aspects, time-lapse imaging parameters including, for example, compaction and/or cavitation and/or expansion and/or collapse parameters of an embryo are measured to arrive at a parameter measurement is employed to provide a determination of the likelihood of the euploid embryo to implant into a uterus. In some embodiments, the compaction and/or cavitation and/or expansion and/or collapse parameter is a morphological event is measured by time-lapse microscopy. In another embodiment, clinical variables such as patient age, number of eggs retrieved and fertilization rate are used in conjunction with time lapse imaging parameters including, for example, compaction and/or cavitation and/or expansion and/or collapse parameters of an embryo to determine the likelihood of the euploid embryo to implant to a uterus.

One aspect of the invention provides methods for ranking the likelihood of a euploid embryo or blastocyst to implant into a uterus or result live birth among a patient's available euploid embryos or blastocysts. In one embodiment, the probability of selecting a euploid embryo with highest implantation potential is maximized for patients with more than one euploid embryos to choose from. In some aspects of the invention, methods are provided for ranking the likelihood that a euploid embryo will implant into a uterus. In such aspects, time-lapse imaging parameters including, for example, compaction and/or cavitation and/or expansion and/or collapse parameters of an embryo are measured to arrive at a parameter measurement which is employed to provide ranking of the likelihood of the embryo to be euploid or become a euploid blastocyst. In a further embodiment, the determination is used to select the embryo with highest likelihood being euploid for transfer. In some embodiments, the compaction and/or cavitation and/or expansion and/or collapse parameter is a morphological event that is measurable by time-lapse microscopy. In a further embodiment, clinical variables such as patient age, number of eggs retrieved and fertilization rate are used together with time-lapse imaging parameters including, for example, compaction and/or cavitation and/or expansion and/or collapse parameters of an embryo are measured to arrive at a parameter measurement which is employed to provide ranking of the likelihood of the embryo to be euploid or become a euploid blastocyst.

In another aspect of the invention, methods are provided for determining the likelihood that a patient will become pregnant and/or miscarry upon transfer of one or more human embryos determined to have good developmental potential and/or be euploid. In certain embodiments, the method includes measuring the duration of compaction, cavitation, expansion and/or collapse. In certain aspects, the method includes the steps of culturing one or more embryos under conditions sufficient for embryo development; time lapse imaging said one or more embryos; and analyzing one or more image features, thereby determining (1) an onset of compaction, cavitation, expansion or collapse and (2) a resolution of compaction, cavitation, expansion and/or collapse. In one embodiment, the duration of blastocyst expansion and collapse is determined. In a further embodiment, the one or more image feature is area defined by embryo outer boundary. In another embodiment, the method further comprises measuring one or more cellular parameters selected from the duration of expansion; the duration of collapse; the time interval between expansion and collapse, the frequency of collapse, the rate of expansion; the rate of collapse, average embryo size after initial expansion, the degree of expansion, and the degree of collapse.

In another embodiment, methods are provided for determining the likelihood that a patient will have at least one euploid blastocyst. In one embodiment, the method comprises measuring the duration of compaction, cavitation, expansion and/or collapse comprises the steps of culturing one or more embryos under conditions sufficient for embryo development; time lapse imaging said one or more embryos; and analyzing one or more image features, thereby determining (1) an onset of compaction, cavitation, expansion or collapse and (2) a resolution of compaction, cavitation, expansion and/or collapse. In one embodiment, the duration of blastocyst expansion and collapse is determined. In a further embodiment, the one or more image feature is area defined by embryo outer boundary. In another embodiment, the method further comprises measuring one or more cellular parameters selected from the duration of expansion; the duration of collapse; the time interval between expansion and collapse, the frequency of collapse, the rate of expansion; the rate of collapse, average embryo size after initial expansion, the degree of expansion, and the degree of collapse.

In another embodiment, a method for classifying a human embryo based on its relative likelihood of being aneuploid is provided. In one aspect the method includes culturing one or more human embryos under conditions sufficient for embryo development, time lapse imaging the one or more embryos, analyzing one or more image features to determine the average size of the embryo after initial expansion (Pexp-area) and/or the time between the second and third cytokinesis (P3) and/or the time from first cleavage to cavitation (tCav) and classifying the embryo into categories 1-5 based on the relative likelihood of the embryo being aneuploid. In one embodiment, a naïve Bayesian classifier is used to classify the embryos. In another embodiment, a SVM classifier is used to classify the embryos. In still another embodiment, a Random Forest classifier is used to classify the embryo. In still another embodiment, a Boosting Tree classifier is used to classify the embryo. In still another embodiment a combination of two or more of a naïve Bayesian classifier, an SVM classifier, a Random Forest classifier and a Boosting Tree classifier is used to classify the embryo. In one embodiment, the number of pronuclei (#2PN) and age are also used to classify the embryo. In a particular embodiment, #2PN, tCav and Psyn are used to classify the human embryo based on its relative likelihood of being aneuploid. In another particular embodiment, Pexp-area, Age and P3 are used to classify the embryo based on its relative likelihood of being aneuploid.

In another embodiment, an automated system is provided for assessing human developmental potential or the likelihood of an embryo being euploid. In one embodiment the automated system comprises an incubator, one or more microscopes configured in the incubator, a computer comprising software for capturing sequential images from the one or more microscopes over a period of up to 5 days of human embryo development, software for determining a plurality of cellular activity parameters and software for employing the plurality of parameters to determine the developmental potential of the embryo or the likelihood that the embryo will be euploid. In one embodiment, each microscope configured in the incubator comprises a multi-well culture dish positioned for imaging and a camera capable of capturing images of human embryos in the microwell culture dish. In one embodiment the software for determining a plurality of cellular parameters determines or more of duration of expansion, duration of collapse, degree of expansion, degree of collapse, rate of expansion, rate of collapse, average embryo size after initial expansion and the time interval between expansion and collapse. In a further embodiment, the cellular parameters further comprise a cell division parameter based on the interval between the interval between the first and second cytokinesis of the human embryo and/or a cell parameter based on interval between the second and third cytokinesis of the human embryo. In a particular embodiment the cell division parameter is P2 or P3.

In another embodiment, the automated system for assessing human embryo developmental potential or likelihood of embryo being euploid in vitro provided comprises and incubator, one or more microscopes configured in the incubator each comprising a multiwell culture dish positioned for imaging and a camera capable of capturing images of human embryos in the multiwell culture dish; and a computer comprising software for capturing sequential images from the one or more microscopes over a period of up to 5 days of human embryo development, software for determining a plurality of cellular activity parameters and software for employing said plurality of parameters to classify the human embryo for developmental potential of the embryo or for the likelihood of the human embryo being euploid. In one embodiment, the plurality of cellular parameters comprises one or more of the average size of the embryo after initial expansion (Pexp-area), the time between the second and third cytokinesis (P3), the time from syngamy to the first cytokinesis (Psyn) and the time from first cleavage to cavitation (tCav). In one embodiment, #2PN and Age are further used in combination with the one or more images features to classify the embryo. In another embodiment, Age, #2PN, tCav and Psyn are used to classify the human embryo. In one embodiment, Pexp-area, Age and P3 are used to classify the human embryo.

In another embodiment, a method is provided for determining the likelihood that a euploid embryo will implant into the uterus of a female. In one embodiment, the method includes culturing one or more embryos under conditions sufficient for embryo development; time lapse imaging said one or more embryos; and analyzing one or more image features thereby determining (1) the percentage of time the embryo spends in expansion (Exp Time), and/or (2) the average time that the embryo spends in each expansion event (Avg. Exp. Time) employing said image features to determine the likelihood that the human euploid embryo will implant into the uterus of said female. In one embodiment, the method includes first determining that an embryo is Euploid. In one embodiment, the method for first determining that an embryo is euploid comprises measuring the duration of compaction, cavitation, expansion and/or collapse comprises the steps of culturing one or more embryos under conditions sufficient for embryo development; time lapse imaging said one or more embryos; and analyzing one or more image features, thereby determining (1) an onset of compaction, cavitation, expansion or collapse and (2) a resolution of compaction, cavitation, expansion and/or collapse. In one embodiment, the duration of blastocyst expansion and collapse is determined. In a further embodiment, the one or more image feature is area defined by embryo outer boundary. In another embodiment, the method further comprises measuring one or more cellular parameters selected from the duration of expansion; the duration of collapse; the time interval between expansion and collapse, the frequency of collapse, the rate of expansion; the rate of collapse, average embryo size after initial expansion, the degree of expansion, and the degree of collapse. In a further embodiment, the human embryo is first determined to be euploid by culturing one or more human embryos under conditions sufficient for embryo development, time lapse imaging said one or more human embryos, analyzing one or more image features thereby determining the average size of the embryo after initial expansion (Pexp-area), and/or the time between the second and third cytokinesis (P3) and/or the time from syngamy to the first cytokinesis (Psyn) and/or the time from first cleavage to cavitation (tCav), and classifying the embryo based on its likelihood of being euploid. In another embodiment, the euploid human embryo is first determined to be euploid by pre-implantation genetic screening (PGS).

In one embodiment, the human euploid embryo is determined to be more likely to implant if the Exp Time is greater than about 85% or 86% or 87% or 88% or 89% or 90%. In another embodiment, the euploid embryo is determined to be less likely to implant if the Exp time is less than about 85%. In one embodiment, the euploid embryo is determined to be more likely to implant if the Avg Exp Time is at least about 120 minutes, 125 minutes 130 minutes, or 135 minutes or longer. In another embodiment, a euploid embryo is determined to be less likely to implant if the Avg Exp Time is less than about 120 min or less than about 115 minutes. In another embodiment, the method provides measuring one or more additional cellular parameters selected from the group consisting of the parameters listed in tables 1 or 2.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 8 shows that the time from the first cleavage to cavitation is predictive of aneuploidy in human embryos.

FIG. 11 shows by four different classifiers that embryo age combined with average size after initial expansion and P3 are indicative of aneuploidy in human embryos and can be classified into five categories of increasing risk of aneuploidy.

DETAILED DESCRIPTION OF THE INVENTION

Figure 1:
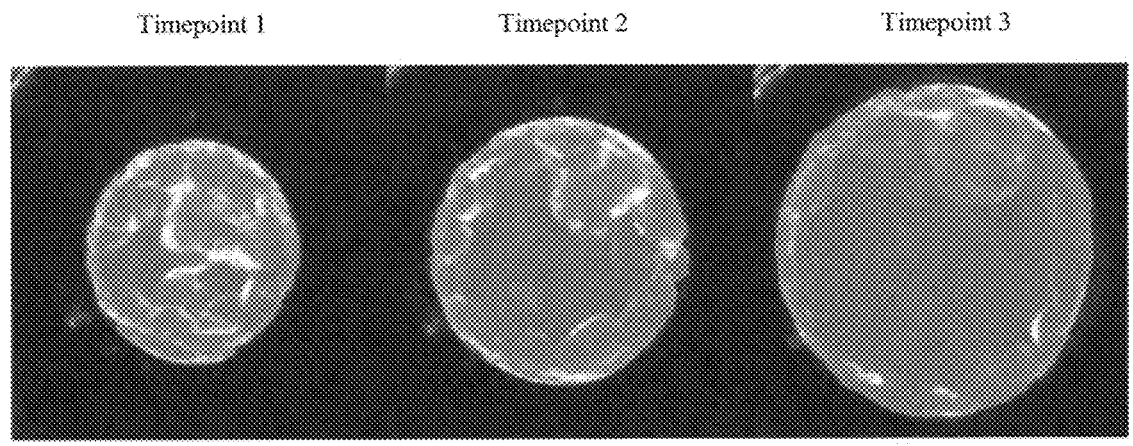
FIG. 1 is a series of time-lapse images that depicts the embryo outer boundary segmentation from three time points for the same embryo undergoing blastocyst expansion.

Before the present methods and compositions are described, it is to be understood that this invention is not limited to any particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods are provided herein for quantitatively assessing dynamic changes of human embryo morphology at the morula and/or blastocyst stage (e.g., compaction, cavitation, expansion and collapse) using imaging features. The disclosed methods provide quantitative tools that enable semi-automatic or automatic measurement of morula and/or blastocyst stage developmental events and provide an objective, standardized measurement guideline for the kinetic morula and/or blastocyst stage events.

Methods, compositions and kits for determining the likelihood of reaching the blastocyst stage and/or implanting into the uterus and/or being born live are also provided. These methods, compositions and kits find use in identifying embryos in vitro that are most useful in treating infertility in humans. These and other objects, advantages, and features of the invention will become apparent to those persons skilled in the art upon reading the details of the subject methods and compositions as more fully described below.

The terms "developmental potential' and "developmental competence' are used herein to refer to the ability or capacity of a healthy embryo or to grow or develop. The terms may refer to the ability or capacity of a healthy embryo to reach the blastocyst stage, or develop into a good quality blastocyst, implant into the uterus, and/or be born live.

The term "specificity" when used herein with respect to prediction and/or evaluation methods is used to refer to the ability to predict or evaluate an embryo for determining the likelihood that the embryo will not develop into a blastocyst or will or will not be euploid by assessing, determining, identifying or selecting embryos that are not likely to reach the blastocyst stage and/or implant into the uterus and/or are aneuploid. High specificity as used herein refers to where at least about 70%, 72%, 75%, 77%, 80%, 82%, 85%, 88%, 90%, 92%, 95% or more, or 100% of the human embryos not selected are not likely to reach the blastocyst stage and/or implant into the uterus and/or are aneuploid. In some embodiments, embryos that are not likely to reach the blastocyst stage and/or implant and/or are aneuploid into the uterus stage are deselected.

Figure 16:
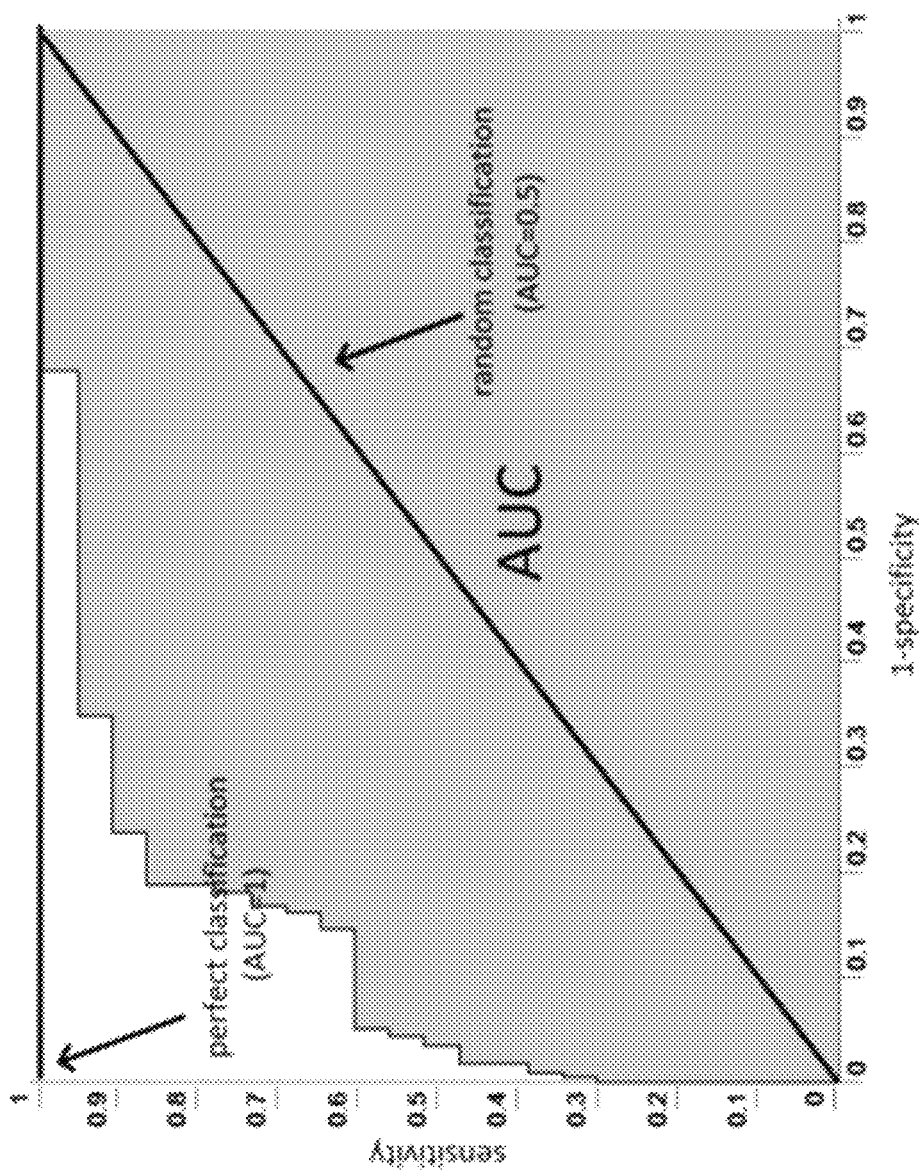
FIG. 16 shows one exemplary embodiment of area under curve.

The term "AUC" or "area under curve" when used herein with respect to prediction and/or evaluation methods is used to refer to the performance of the prediction method (i.e. the probability that the predication method will rank a randomly chosen euploid embryo or euploid blastocyst higher than a randomly chosen aneuploid embryo or aneuploidy blastocyst). AUC is calculated from the receiver operating characteristic (ROC) and is equal to the probability that a classifier will rank a randomly chosen positive instance higher than a randomly chosen negative one. The AUC can be calculated to characterize the performance for a number of different classifiers including, without limitation, Naïve Bayesian, SVM, Random Forest and Boosting Tree. Any one of which alone or in combination may be used to classify embryos based on one or more cellular parameters. An example of AUC is shown in FIG. 16.

The term odds ratio (OR) when used herein with respect to prediction and/or evaluation methods is used to refer to a measure of the effectiveness of the prediction method. OR=(TP/FN)/(FP/TN); where TP, FN, FP and TN are the number of true positives, false negatives, false positives and true negatives respectively.

The term "embryo" is used herein to refer both to the zygote that is formed when two haploid gametic cells, e.g. an unfertilized secondary oocyte and a sperm cell, unite to form a diploid totipotent cell, e.g. a fertilized ovum, and to the embryo that results from the immediately subsequent cell divisions, i.e. embryonic cleavage, up through the morula, i.e. 16-cell stage and the blastocyst stage (with differentiated trophectoderm and inner cell mass).

The term "blastocyst" is used herein to describe all embryos that reach cavitation (i.e., the formation of cavities).

The terms "born live" or "live birth" are used herein to include but are not limited to healthy and/or chromosomally normal (normal number of chromosomes, normal chromosome structure, normal chromosome orientation, etc.) births.

The term "arrested" is used herein to refer to any embryo that does not meet the definition of blastocyst.

The term "oocyte" is used herein to refer to an unfertilized female germ cell, or gamete. Oocytes of the subject application may be primary oocytes, in which case they are positioned to go through or are going through meiosis I, or secondary oocytes, in which case they are positioned to go through or are going through meiosis II.

By "meiosis" it is meant the cell cycle events that result in the production of gametes. In the first meiotic cell cycle, or meiosis I, a cell's chromosomes are duplicated and partitioned into two daughter cells. These daughter cells then divide in a second meiotic cell cycle, or meiosis II, that is not accompanied by DNA synthesis, resulting in gametes with a haploid number of chromosomes.

By a "mitotic cell cycle", it is meant the events in a cell that result in the duplication of a cell's chromosomes and the division of those chromosomes and a cell's cytoplasmic matter into two daughter cells. The mitotic cell cycle is divided into two phases: interphase and mitosis. In interphase, the cell grows and replicates its DNA. In mitosis, the cell initiates and completes cell division, first partitioning its nuclear material, and then dividing its cytoplasmic material and its partitioned nuclear material (cytokinesis) into two separate cells.

By a "first mitotic cell cycle" or "cell cycle 1" it is meant the time interval from fertilization to the completion of the first cytokinesis event or first mitosis, i.e. the division of the fertilized oocyte into two daughter cells. In instances in which oocytes are fertilized in vitro, the time interval between the injection of human chorionic gonadotropin (HCG) (usually administered prior to oocyte retrieval) to the completion of the first cytokinesis event may be used as a surrogate time interval.

"P1" or "P1 duration" is used herein to refer to the time interval between the appearance of the first cleavage furrow to completion of the $1^{st}$ cell division or first cytokinesis event.

"$1^{st}$ cytokinesis phenotype" or "P1 phenotype" is used herein to refer to the cellular, biochemical and/or morphological characteristics of an embryo prior to completing P1 (i.e. the cellular, physical, biochemical and/or morphological characteristics of an embryo prior to completing the $1^{st}$ cell division or first cytokinesis event).

"Abnormal P1 phenotype" or "$A1^{cyto}$" is used herein to refer to uncharacteristic cellular, biochemical and/or morphological events of an embryo prior to completing P1 (i.e. prior to completing the $1^{st}$ cell division or first cytokinesis event) when compared to a reference or control embryo having a high likelihood of reaching blastocyst, becoming a good quality blastocyst and/or implanting into the uterus. "Abnormal P1 phenotype" or "$A1^{cyto}$" as used herein includes oolemma ruffling, membrane ruffling, and/or formation of one or more pseudo cleavage furrows before the initiation and/or completion of P1 (the time interval between the appearance of the first cleavage furrow to completion of the $1^{st}$ cell division or first cytokinesis event).

By a "second mitotic cell cycle" or "cell cycle 2" or "P2" it is meant the second cell cycle event observed in an embryo, the time interval between the production of daughter cells from a fertilized oocyte by mitosis and the production of a first set of granddaughter cells from one of those daughter cells (the "leading daughter cell", or daughter cell A) by mitosis. P2 also encompasses the duration of time that the embryo is a 2 cell embryo, that is the duration of the 2 cell stage. Cell cycle 2 may be measured using several morphological events including the end of cytokinesis 1 and the beginning of cytokinesis 2, or the end of cytokinesis 1 and the end of cytokinesis 2 or the beginning of cytokinesis 1 and the beginning of cytokinesis 2 or the beginning of cytokines 1 and the end of cytokinesis 2 or the end of mitosis 1 and the beginning of mitosis 2 or the end of mitosis 1 and the end of mitosis 2 or the beginning of mitosis 1 and the beginning of mitosis 1 or the beginning of mitosis 1 and the end of mitosis 2. Upon completion of cell cycle 2, the embryo consists of 3 cells. In other words, cell cycle 2 can be visually identified as the time between the embryo containing 2-cells and the embryo containing 3-cells.

By a "third mitotic cell cycle" or "cell cycle 3" or "P3" it is meant the third cell cycle event observed in an embryo, typically the time interval from the production of a first set of grandaughter cells from a fertilized oocyte by mitosis and the production of a second set of granddaughter cells from the second daughter cell (the "lagging daughter cell" or daughter cell B) by mitosis. Cell cycle 3 may be measured using several morphological events including the end of cytokinesis 2 and the beginning of cytokinesis 3, or the end of cytokinesis 2 and the end of cytokinesis 3 or the beginning of cytokinesis 2 and the beginning of cytokinesis 3 or the beginning of cytokinesis 2 and the end of cytokinesis 3 or the end of mitosis 3 and the beginning of mitosis3 or the end of mitosis 2 and the end of mitosis3 or the beginning of mitosis 2 and the beginning of mitosis 3 or the beginning of mitosis 2 and the end of mitosis 3. In other words, cell cycle 3 can be visually identified as the time between the embryo containing 3-cells and the embryo containing 4-cells.

By "first cleavage event" or "first cleavage", it is meant the first division, i.e. the division of the oocyte into two daughter cells, i.e. cell cycle 1. Upon completion of the first cleavage event, the embryo consists of 2 cells.

By "second cleavage event" or "second cleavage", it is meant the second set of divisions, i.e. the division of leading daughter cell into two granddaughter cells and the division of the lagging daughter cell into two granddaughter cells. In other words, the second cleavage event consists of both cell cycle 2 and cell cycle 3. Upon completion of second cleavage, the embryo consists of 4 cells.

By "third cleavage event", it is meant the third set of divisions, i.e. the divisions of all of the granddaughter cells. Upon completion of the third cleavage event, the embryo typically consists of 8 cells.

By "cytokinesis" or "cell division" it is meant that phase of mitosis in which a cell undergoes cell division. In other words, it is the stage of mitosis in which a cell's partitioned nuclear material and its cytoplasmic material are divided to produce two daughter cells. The period of cytokinesis is identifiable as the period, or window, of time between when a constriction of the cell membrane (a "cleavage furrow") is first observed and the resolution of that constriction event, i.e. the generation of two daughter cells. The initiation of the cleavage furrow may be visually identified as the point in which the curvature of the cell membrane changes from convex (rounded outward) to concave (curved inward with a dent or indentation). This is illustrated for example in FIG. 4 of U.S. Pat. No. 7,963,906 top panel by white arrows pointing at 2 cleavage furrows. The onset of cell elongation may also be used to mark the onset of cytokinesis, in which case the period of cytokinesis is defined as the period of time between the onset of cell elongation and the resolution of the cell division.

By "first cytokinesis" or "cytokinesis 1" it is meant the first cell division event after fertilization, i.e. the division of a fertilized oocyte to produce two daughter cells. First cytokinesis usually occurs about one day after fertilization.

By "second cytokinesis" or "cytokinesis 2", it is meant the second cell division event observed in an embryo, i.e. the division of a daughter cell of the fertilized oocyte (the "leading daughter cell", or daughter A) into a first set of two granddaughters.

By "third cytokinesis" or "cytokinesis 3", it is meant the third cell division event observed in an embryo, i.e. the division of the other daughter of the fertilized oocyte (the "lagging daughter cell", or daughter B) into a second set of two granddaughters.

The term "fiduciary marker" or "fiducial marker," is an object used in the field of view of an imaging system which appears in the image produced, for use as a point of reference or a measure. It may be either something placed into or on the imaging subject, or a mark or set of marks in the reticle of an optical instrument.

The term "micro-well" refers to a container that is sized on a cellular scale, preferably to provide for accommodating eukaryotic cells or a single oocyte or embryo.

The term "selecting" or "selection" refers to any method known in the art for moving one or more embryos, blastocysts or other cell or cells as described herein from one location to another location. This can include but is not limited to moving one or more embryos, blastocysts or other cell or cells within a well, dish or other compartment or device so as to separate the selected one or more embryos, blastocysts or other cell or cells of the invention from the non- or deselected one or more embryos of the invention (such as for example moving from one area of a well, dish, compartment or device to another area of a well, dish, compartment or device). This can also include moving one or more embryos, blastocysts or other cell or cells from one well, dish, compartment or device to another well, dish, compartment or device. Any means known in the art for separating or distinguishing the selected one or more embryos, blastocysts or other cell or cells from the non- or deselected one or more embryos, blastocysts or other cell or cells can be employed with the methods of the present invention. In one embodiment, selected embryos are selected for transfer to a recipient for gestation. In another embodiment, selected embryos are selected for freezing for potential future implantation. In another embodiment, embryos are selected for continued culture. In another embodiment, embryos are selected for further evaluation by other methods such as preimplantation genetic testing, genomics, proteonomics, and/or secretomics.

The term "deselected" or "deselection" as used herein refers to embryos with poor developmental potential which are not chosen for implantation or are chosen for non-implantation. In some embodiments, deselected embryos are not transferred or implanted into the uterus. For example, an embryo at high risk for aneuploidy is deselected.

After fertilization both gametes contribute one set of chromosomes (haploid content), each contained in a structured referred to herein as a "pronucleus" ("PN") After normal fertilization, each embryo shows two pronuclei (PNs), one representing the paternal genetic material and one representing the maternal genetic material. "Syngamy" as used herein refers to the breakdown of the pronuclei (PNs) when the two sets of chromosomes unite, occurring within a couple hours before the first cytokinesis.

The time parameter "$P_{syn}$" or "S" or "$P_{M1}$", as used interchangeably herein, refers to a parameter defined by the time from syngamy to the beginning of the first cytokinesis. Sometimes it is not possible to visualize PN or to measure syngamy, such embryos are said to have "unmeasurable syngamy" or "US." Additionally, it is possible that an embryo will show atypical syngamy patterns or timing. Such embryos are said to have "abnormal syngamy" or "AS." AS embryos show disordered PNs movement within the cytoplasm without prompt dispersion of nuclear envelopes and typically have a shorter $P_{syn}$ when compared to normal syngamy or "NS" embryos. This may be visualized by time lapse microscopy when the PN move unsteadily within the cytoplasm either together or separately before their disappearance. AS embryos often also show active oolema movement before the dispersion of the nuclear envelopes. NS embryos on the other hand, show timely disappearance of PNs with a smooth dispersion of the nuclear envelopes with minimal or no pronuclear movement within the cytokplasm and minimal or no oolema movement prior to the dispersion of nuclear envelopes.

The parameter "AC" as used herein refers to abnormal cleavages wherein more than two cells originate from a single cleavage. For example, when one blastomere gives rise to more than two daughter cells, the embryo is referred to as an AC embryo or the embryo is said to display AC. By "AC1" is meant that the AC phenotype happens at the first cleavage. In an AC1 embryo a single cell embryo divides once and gives rise to a three or more cell embryo (e.g. 1→3 cells) (FIG. 4A). By "AC2" is meant that the AC phenotype happens at the second cleavage. In an AC2 embryo, a single blastomere divides to give rise to three or more cells (e.g. 1→4 cells) (FIG. 4B) during the second cleavage. By "AC3" is meant that the AC phenotype happens at the third cleavage. In an AC3 embryo, a single blastomere of a three cell embryo divides to give rise to three or more cells. AC can happen at any cleavage, and/or during more than one cleavage event. For example, an AC1 embryo (e.g. 1→3 cells) can also display AC2 (e.g. 3→5 cells).

The term #2PN herein refers to the number of embryos that formed two pronuclei after fertilization of a cohort of eggs in vitro. #2PN is related to the number of eggs retrieved from a particular patient or donor and the success rate of the in vitro fertilization (IVF) or intracytoplasmic sperm injective (ICSI) process. For example, if 10 eggs are retrieved from a patient or donor, IVF or ICSI are performed, and 7 eggs are fertilized and formed embryos with two pronuclei, #2PN would be 7.

The term "compaction" refers to the joining of the outer cells of the embryo by intercellular connections, such as tight junctions, gap junctions and desmosomes, beginning at about the 8 cell stage. Compaction results in a compact sphere of tightly bound cells of the morula stage. During compaction, the boundaries of individual cells become less distinguishable.

The term "cavitation" refers to the process that begins when the outer layer of cells of the morula begin secreting fluid that creates a cavity, thus forming a blastocyst comprising an outer trophectoderm and an inner cell mass.

The term "blastocyst expansion" or "expansion" refers to the process wherein the volume, or size, of the blastocyst increases. In contrast, the term "blastocyst collapse" or "collapse" refers to a decrease in the volume or the size of a blastocyst. A blastocyst may repeat expansion and collapse one or more times.

The term "euploid" is used herein to refer to a cell that contains an integral multiple of the haploid, or monoploid, number. For example, a human autosomal cell having 46 chromosomes is euploid, and a human gamete having 23 chromosomes is euploid. By "euploid embryo" it is meant that the cells of the embryo are euploid.

The term "aneuploid" is used herein to refer to a cell that contains an abnormal number of chromosomes. For example, a cell having an additional chromosome, or a part of a chromosome, and a cell missing a chromosome, or a part of a chromosome, are both aneuploid. By "aneuploid embryo" it is meant that one or more cells of an embryo are aneuploid. By "aneuploid chromosome" is meant a chromosome that has more or less than two copies. For example, chromosome 21 is aneuploid in embryos with trisomy 21. Aneuploid embryos are not chromosomally normal and have low developmental potential.

By the term "monosomy" is meant an aneuploidy where a specific chromosome is present in only one copy. By "trisomy" is meant an aneuploidy where a specific chromosome is present in three copies.

The term "complex aneuploidy" is used herein to refer to aneuploidies in which 2 or more, for example 3 or more, or 4 or more or 5 or more or more than 6, chromosomes are affected. A complex aneuploidy can be a mixture of monosomies and trisomy. For example, a complex aneuploidy may comprise both trisomy 21 and monosomy 17, or any other combination of monosomies or trisomies.

The term "non-viable aneuploidy" is used herein to refer to aneuploidies which, when present, do not result in a viable embryo. Examples of "non-viable aneuploidies" include, without limitation, trisomy 2 and/or monosomy 1.

The term "disease causing aneuploidy" is meant those aneuploidies which may, but not necessarily, give rise to viable embryos, but for which a disease is associated. Examples of disease causing aneuploidies include, without limitation, trisomy 21 (Down syndrome), Trisomy 18 (Edward's syndrome), Trisomy 13 (Patau syndrome), Trisomy 16, Trisomy 22, and sex chromosome aneuploidies including, but not limited to monosomy X or 45X (Turner syndrome) and XXY or 47XXY (Klinefelter syndrome)

The focus of prior patents and applications including U.S. Pat. Nos. 7,963,906; 8,323,177; 8,337,387 and PCT Appl. No. WO 2012/163363 each center primarily around selection criteria for human embryos in in vitro fertilization. While these patents/applications each discuss determining whether embryos have good or poor developmental potential (i.e. are likely or not to develop as desired), the timing parameters described therein are typically used in the clinic in large part to select embryos with good developmental potential. In contrast, the methods of the current invention center around the morula and/or blastocyst stage kinetic events (e.g., compaction, cavitation, expansion and collapse) using imaging features, and the morula and/or blastocyst stage parameters may be used to deselect human embryos and target them for non-transfer in in vitro fertilization treatment. These parameters may be used alone or in combination with the selection parameters described in U.S. Pat. Nos. 7,963,906; 8,323,177; 8,337,387 and PCT Appl. No. WO 2012/163363. For example, once an embryo is determined to have good developmental potential by the methods of U.S. Pat. Nos. 7,963,906; 8,323,177; 8,337,387 and PCT Appl. No. WO 2012/163363, that embryo may be further analyzed for one or more of the novel compaction, cavitation, expansion and collapse parameters described herein to further increase the sensitivity and specificity of the claimed methods.

The deselection criteria of the current invention include prolonged or shortened duration of compaction, cavitation, expansion and collapse as well as the parameters listed in Table 1.

TABLE 1

| Expansion/Collapse Derived Parameters | |
|---|---|
| Parameter | Parameter Description |
| Freq Collapse (avg) | Average time between collapse events |
| Frequency Collapse (total) | Number of collapse events/time since start of expansion |
| Exp/Col Time | Total expansion time/Total collapse time |
| Exp Time | % total time spent in expansion |
| Avg Exp Time | Average time spent in each expansion event |
| Avg Exp/col Time | Average time spent in expansion/average time spent in collapse per event |
| Exp Rate (Total) | Expansion rate (total area change/total time in expansion) |
| Exp Rate (Avg) | Expansion rate (average area change per event/average time per event) |
| Exp Rate (Std) | Expansion rate (standard deviation of Expansion rate (average)) |
| Col Rate (Total) | Collapse rate (total area change/total time collapse) |
| Col Rate (Avg) | Collapse rate (average area change/average time collapse per event) |
| Col Rate (Std) | Collapse rate (standard deviation of Collapse rate (average)) |

TABLE 1-continued

Expansion/Collapse Derived Parameters

| Parameter | Parameter Description |
|---|---|
| Max Degree Exp | Max degree of expansion (percent area change) |
| Avg Degree Exp | Average degree of expansion |
| Std Degree Exp | Standard deviation of degree of expansion |
| Rate Degree Exp | Rate of degree of expansion (total percent area change/total time) |
| Avg Rate Exp | Average rate of expansion (average percent area change/average time) |
| Std Rate Exp | Standard rate of expansion (standard average rate) |
| Avg Degree Col | Average degree of collapse |
| Std Degree Col | Standard deviation of degree of collapse |
| Rate Degree Col | Rate of collapse degree (total percent area change/total time) |
| Avg Rate Col | Average rate of collapse (average percent area change/average time) |
| Std Rate Col | Standard deviation of rate of collapse (standard deviation of average rate) |
| Time Blast to Exp | Time from blastocyst to expansion, in minutes |
| Time P1st to Exp | Time from first cleavage to expansion, in minutes |
| Avg last 6 frames area | Average area, last 6 frames |
| tCav | Time from first cleavage to cavitation |
| Pexp-area | Average embryo size after initial expansion |

Any one of the parameters listed in Table 1 may be used alone or in combination with each other or other cellular parameters including the previously described criteria parameters including, but not limited to those described in Table 2. For the parameters disclosed in both Table 1 and Table 2 and throughout the specification, unless specified, "time from" is used to encompass both time from insemination to the stated time parameter or time from the first cleavage to the stated parameter. For example, parameter t5 below in Table 2, while it is described in the table as being time from ICSI to a 5 cell embryo, this parameter also contemplates time from first cytokinesis to a 5 cell embryo. Similarly, the parameter tCav described above in Table 1 is described as being time from first cleavage to cavitation but also encompasses the time from insemination to cavitation.

TABLE 2

List of Parameters

| Parameter | Description/Reference describing Parameter |
|---|---|
| P1 | Duration of $1^{st}$ cytokinesis |
| P1 Phenotypes ($A1^{cyt}$) | Membrane ruffling, oolemma ruffling and/or formation of one or more pseudo cleavage furrows prior to completing the first cytokinesis (P1) |
| P2 | Interval between $1^{st}$ and $2^{nd}$ cytokinesis (time from 2-cell embryo to 3-cell embryo) (end of $1^{st}$ cytokinesis to end of $2^{nd}$ cytokinesis) (duration as 2 cell embryo) (t3-t2) |
| P3 | Interval between $2^{nd}$ and $3^{rd}$ cytokinesis (time from 3-cell embryo to 4-cell embryo) (end of $2^{nd}$ cytokinesis to end of $3^{rd}$ cytokinesis) (duration as 3 cell embryo) (t4-t3) (synchrony between 3 and 4 cells) |
| $P_{syn}$ | Time from syngamy to $1^{st}$ cytokinesis (appearance of the first cytokinetic cleavage furrow) |
| 2ce-3C | End of $1^{st}$ cleavage to beginning of second cleavage |
| 3C-4C | Beginning of $2^{nd}$ Cleavage to end of $3^{rd}$ Cleavage |
| t5 | Time from ICSI (insemination) to 5 cell embryo |
| 2Cb | Time from insemination to beginning of $1^{st}$ cleavage |
| 2Ce | Time from insemination until end of $1^{st}$ cleavage |
| 3C | Time from insemination to beginning of $2^{nd}$ cleavage |
| 4C | Time from insemination to end of $3^{rd}$ cleavage |
| 5C | Time from insemination to beginning of $4^{th}$ cleavage |
| BL | Formation of blastocoels |
| tM | Time from insemination to morula |
| S3 | Time from 5 cell embryo to 8 cell embryo |
| t2 | Time from insemination to 2 cell embryo |
| t3 | Time from insemination to 3 cell embryo |
| t4 | Time from insemination to 4 cell embryo |
| cc3 | t5-t3: Third cell cycle, duration of period as 3 and 4 cell embryo |
| t5 − t2 | Time to 5 cell embryo minus time to 2 cell embryo |
| cc3/cc2 | Ratio of duration of cell cycle 3 to duration of cell cycle 2 |
| Time till first cleavage | Duration of $1^{st}$ cell cycle |
| 2PB Extrusion | Time from insemination until the second polar body is extruded |
| PN fading | Time from insemination until pronuclei disappear, OR time between the appearance of pronuclei appearing and pronuclei disappearing |
| tSB | Time from insemination to the start of blastulation |
| tSC | Time from insemination to the start of compaction |
| PN appearance | Time from insemination until pronuclei appear |
| t6 | Time from insemination to 6 cell embryo |
| t7 | Time from insemination to 7 cell embryo |
| t8 | Time from insemination to 8 cell embryo |
| cc2b | t4-t2; Second cell cycle for both blastomeres, duration of period as 2 and 3 cell blastomere embryo |
| cc2_3 | t5-t2; Second and third cell cycle, duration of period as 2, 3, and 4 blastomere embryo |
| cc4 | t9-t5; fourth cell cycle; duration of period as 5, 6, 7 and 8 blastomere embryo. |
| s3a | t6-t5; Duration of the individual cell divisions involved in the development from 4 blastomere embryo to 8 blastomere embryo |

TABLE 2-continued

List of Parameters

| Parameter | Description/Reference describing Parameter |
|---|---|
| s3b | t7-t6; Duration of the individual cell divisions involved in the development from 4 blastomere embryo to 8 blastomere embryo |
| s3c | t8-t7; Duration of the individual cell divisions involved in the development from 4 blastomere embryo to 8 blastomere embryo |
| cc2/cc3 | WO 2012/163363 |
| cc2/cc2_3 | WO 2012/163363 |
| cc3/t5 | WO 2012/163363 |
| s2/cc2 | WO 2012/163363 |
| s3/cc3 | WO 2012/163363 |
| AC1 | Cleavage directly from 1 cell embryo to 3 or more cell embryo |
| AC2 | Cleavage of a daughter cell into more than 2 blastomeres |
| AS | Abnormal syngamy Disordered PN movement within the cytoplasm without prompt dispersion of nuclear envelopes, short time period between syngamy and the beginning of the first cytokinesis ($P_{sym}$), and/or active oolema movement before the dispersion of the nuclear envelopes. Measurable by evaluating the movement of pronuclei and/or pronuclei activity throughout the cytoplasm. |
| MN2 | Multinucleation observed at 2 blastomere stage |
| MN4 | Multinucleation observed at 4 blastomere stage |
| EV2 | Evenness of the blastomeres in the 2 blastomere embryo |
| Mul | Multinucleation |
| Uneven or UBS | Uneven sizes of blastomeres at 2-4 cells |
| Frg | Fragmentation |
| Nec | Blastomere necrosis |
| Vac | Vacuolization |
| Age | Age of the egg at time of retrieval (eggs could be retrieved from female patients or donors) |
| #2PN | Number of embryos fertilized that form two pronuclei |

In one embodiment, age, #2PN, tCav, and Psyn are used in combination to determine the likelihood of aneuploidy. In another embodiment, Age, Pexp-area, and P3 are used to determine the likelihood of aneuploidy. In some embodiments, classifiers are used to classify these multi parameter models into one of five categories (1-5 or A-E) wherein embryos in category #1 (or category A) are the most likely to be euploid, while embryos in category 5 (or category E) are most likely to be aneuploid.

In order to utilize single-embryo transfer (SET) in IVF treatment to reduce the risk for adverse outcomes associated with multiple gestation pregnancy, embryologists need a reliable embryo selection method that allows for consistent identification of embryos with the highest developmental potential. Recently, time-lapse analysis of embryo development kinetics has been shown to provide valuable information to improve embryo selection and subsequent pregnancy outcomes. However, previous reports describing morula and/or blastocyst stage events rely on static microscopic images (Filho et al. Hum. Reprod. (2012) 27(9):2641-2648) or use manual video analysis (Iwata et al. Hum. Reprod. (2010) 25(Suppl. 1):141-144; Campbell et al. Reproductive BioMedicine Online, 9 May 2013; and Mazur et al. Hum. Reprod. (2013) 28(Suppl. 1):1149-1206). While these reports correlate human embryo quality and timings of compaction, cavitation, expansion and/or collapse, manual review of time-lapse videos is labor-intensive and time-consuming. Furthermore, manual assessment is subject to high inter- and intra-observer variations. This is especially problematic for time-lapse parameters that involve morula and/or blastocyst stage events (e.g., compaction, cavitation, expansion and collapse), as these events occur in a gradual fashion, and it is difficult for human observers to mark each event beginning and end points in a consistent and reproducible manner. In contrast, the methods of the current invention provide a more quantitative and automatic or semi-automatic measurement to extract timing parameters of embryo developmental kinetics. The methods described herein reduce the inter- and intra-observer variations associated with subjective manual analysis and increase the efficiency of parameter measurement in comparison to manual analysis.

The methods of the current invention also provide for novel selection or deselection cellular parameters for human embryos that can be measured by time lapse microscopy.

In methods of the invention, one or more embryos is assessed for its likelihood to be euploid, and/or reach the blastocyst stage and/or become a good quality blastocyst and/or implant into the uterus and/or be born live by measuring one or more cellular parameters, including compaction, cavitation, expansion and/or collapse parameters, of the embryo(s) and employing these measurements to determine the likelihood that the embryo(s) will reach the blastocyst stage or implant into the uterus. Such parameters have been described, for example, in U.S. Pat. Nos. 7,963,906; 8,323,177, and 8,337,387 and PCT Appl. No.: WO 2012/163363, the disclosure of each of which is incorporated herein by reference in their entirety. The information thus derived may be used to guide clinical decisions, e.g. whether or not to transfer an in vitro fertilized embryo, whether or not to transplant a cultured cell or cells, whether or not to freeze an embryo for later implantation, whether or not to continue to culture the embryo, or whether or not to evaluate the embryo by other methods such as preimplantation genetic testing, genomics, proteonomics, and/or secretomics.

Examples of embryos that may be assessed by the methods of the invention include 1-cell embryos (also referred to as zygotes), 2-cell embryos, 3-cell embryos, 4-cell embryos, 5-cell embryos, 6-cell embryos, 8-cell embryos, etc. typically up to and including 16-cell embryos, morulas, and blastocysts, any of which may be derived by any convenient manner, e.g. from an oocyte that has matured in vivo or from an oocyte that has matured in vitro.

Embryos may be derived from any organism, e.g. any mammalian species, e.g. human, primate, equine, bovine, porcine, canine, feline, etc. Preferably, they are derived from a human. They may be previously frozen, e.g. embryos cryopreserved at the 1-cell stage and then thawed. Alternatively, they may be freshly prepared, e.g., embryos that are freshly prepared (not frozen prior to culturing) from oocytes by in vitro fertilization techniques (fresh or previously frozen oocytes); oocytes that are freshly harvested and/or freshly matured through in vitro maturation techniques (including, e.g., oocytes that are harvested from in vitro ovarian tissue). They may be cultured under any convenient conditions (including different types of culture media) known in the art to promote survival, growth, and/or development of the sample to be assessed, e.g. for embryos, under conditions such as those used in the art of in vitro fertilization; see, e.g., U.S. Pat. Nos. 6,610,543, 6,130,086, 5,837,543, the disclosures of which are incorporated herein by reference; for oocytes, under conditions such as those used in the art to promote oocyte maturation; see, e.g., U.S. Pat. Nos. 5,882,928 and 6,281,013, the disclosures of which are incorporated herein by reference; for stem cells under conditions such as those used in the art to promote maintenance, differentiation, and proliferation, see, e.g. U.S. Pat. Nos. 6,777,233, 7,037,892, 7,029,913, 5,843,780, and 6,200,806, US Application No. 2009/0047263; US Application No. 2009/0068742, the disclosures of which are incorporated herein by reference. Often, the embryos are cultured in a commercially available medium such as KnockOut DMEM, DMEM-F12, or Iscoves Modified Dulbecco's Medium that has been supplemented with serum or serum substitute, amino acids, growth factors and hormones tailored to the needs of the particular embryo being assessed.

In some embodiments, the embryos are assessed by measuring cell parameters by time-lapse imaging. The embryos may be cultured in standard culture dishes. Alternatively, the embryos may be cultured in custom culture dishes, e.g. custom culture dishes with optical quality micro-wells as described herein. In such custom culture dishes, each micro-well holds a single fertilized egg or embryo, and the bottom surface of each micro-well has an optical quality finish such that the entire group of embryos within a single dish can be imaged simultaneously by a single miniature microscope with sufficient resolution to follow the cell mitosis processes. The entire group of micro-wells shares the same media drop in the culture dish, and can also include an outer wall positioned around the micro-wells for stabilizing the media drop, as well as fiducial markers placed near the micro-wells. The media drops can have different volumes. The hydrophobicity of the surface can be adjusted with plasma etching or another treatment to prevent bubbles from forming in the micro-wells when filled with media. Regardless of whether a standard culture dish or a custom culture dish is utilized, during culture, one or more developing embryos may be cultured in the same culture medium, e.g. between 1 and 30 embryos may be cultured per dish. Specific embodiments of culture dishes are described, for example, in U.S. Patent Application Publication No. 2014/0106389, incorporated by reference herein in its entirety. Additional embodiments of culture dishes suitable for use automated time imaging systems are described in U.S. Pat. No. 8,633,017.

Figure 12:
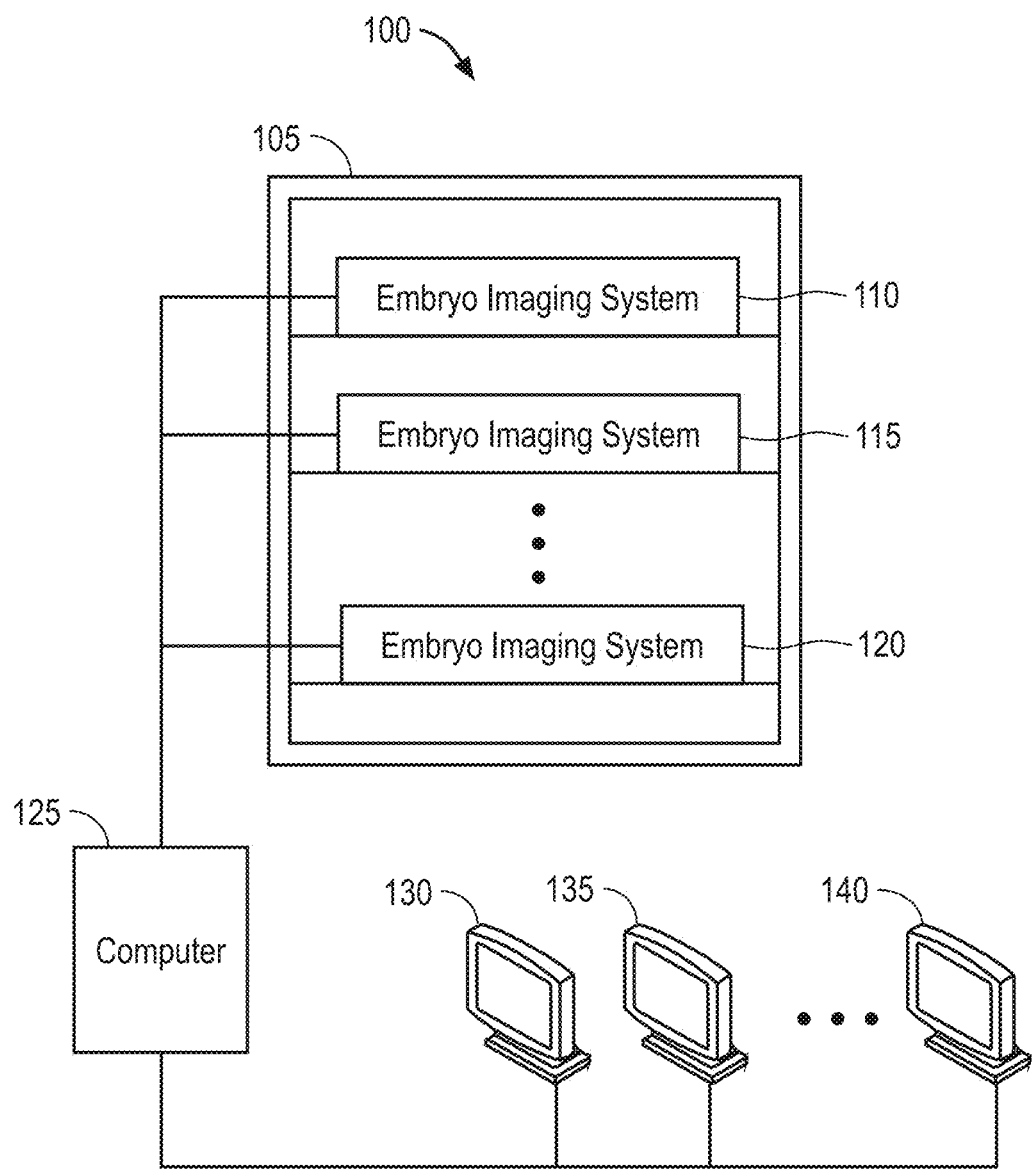
FIG. 12 illustrates a schematic diagram of an apparatus, according to an embodiment of the invention.
Figure 13:
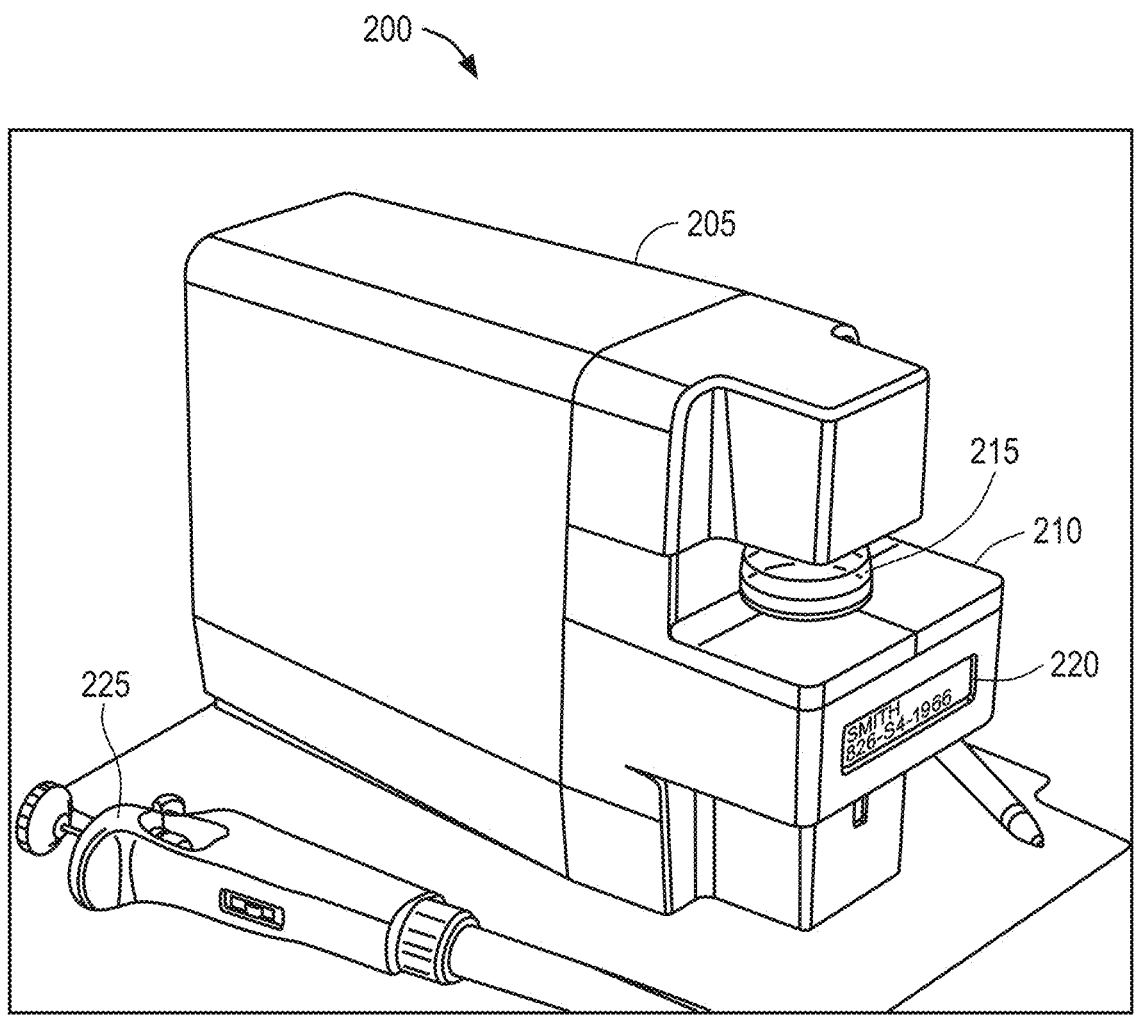
FIG. 13 illustrates a schematic diagram of an imaging system, according to an embodiment of the invention.

Images are acquired over time, and are then analyzed to arrive at measurements of the one or more cellular parameters. Time-lapse imaging may be performed with any computer-controlled microscope that is equipped for digital image storage and analysis, for example, inverted microscopes equipped with heated stages and incubation chambers, or custom built miniature microscope arrays that fit inside a conventional incubator. The array of miniature microscopes enables the concurrent culture of multiple dishes of samples in the same incubator, and is scalable to accommodate multiple channels with no limitations on the minimum time interval between successive image capture. Using multiple microscopes eliminates the need to move the sample, which improves the system accuracy and overall system reliability. The individual microscopes in the incubator can be partially or fully isolated, providing each culture dish with its own controlled environment. This allows dishes to be transferred to and from the imaging stations without disturbing the environment of the other samples. Exemplary preferred imaging systems are described, for example, in U.S. Patent Application Publication No. 2014/0106389, incorporated by reference herein in its entirety. A schematic diagram of an imaging system 200 according to an embodiment of the invention is illustrated in FIG. 13. The imaging system 200 includes a single-channel or multi-channel microscope system including on-board electronics placed inside an outer housing 205. Referring to FIGS. 12 and 13, in one embodiment, the imaging system 200 may communicate with the computer 125. Alternatively, the imaging system 200 may communicate with a controller outside of the incubator 105 and may include a reduced set of on-board electronics. The remainder of the on-board electronics may be included in the controller. Housing 205 may be constructed of non-embryotoxic materials, such as aluminum and plastics. In one embodiment, a loading platform 210 extending outward from the housing 205 allows for a multi-well culture dish 215 to be positioned for imaging by the microscope system. Alternatively, the multi-well culture dish 215 may be loaded in a culture chamber integrated in the housing 205. Embryos may be placed in dish 215 with pipette 225. In one embodiment, the microscope system includes software to monitor the loading of a dish 215 into loading platform 210 and make any adjustments necessary for the proper imaging of the embryos cultured in the dish. Another embodiment of an imaging system to simultaneously monitoring multiple human embryos that is useful for the present invention is described in U.S. Pat. Nos. 8,265,357 and 8,633,017, and U.S. patent publication U.S. 2014/0212911.

Figure 14A:
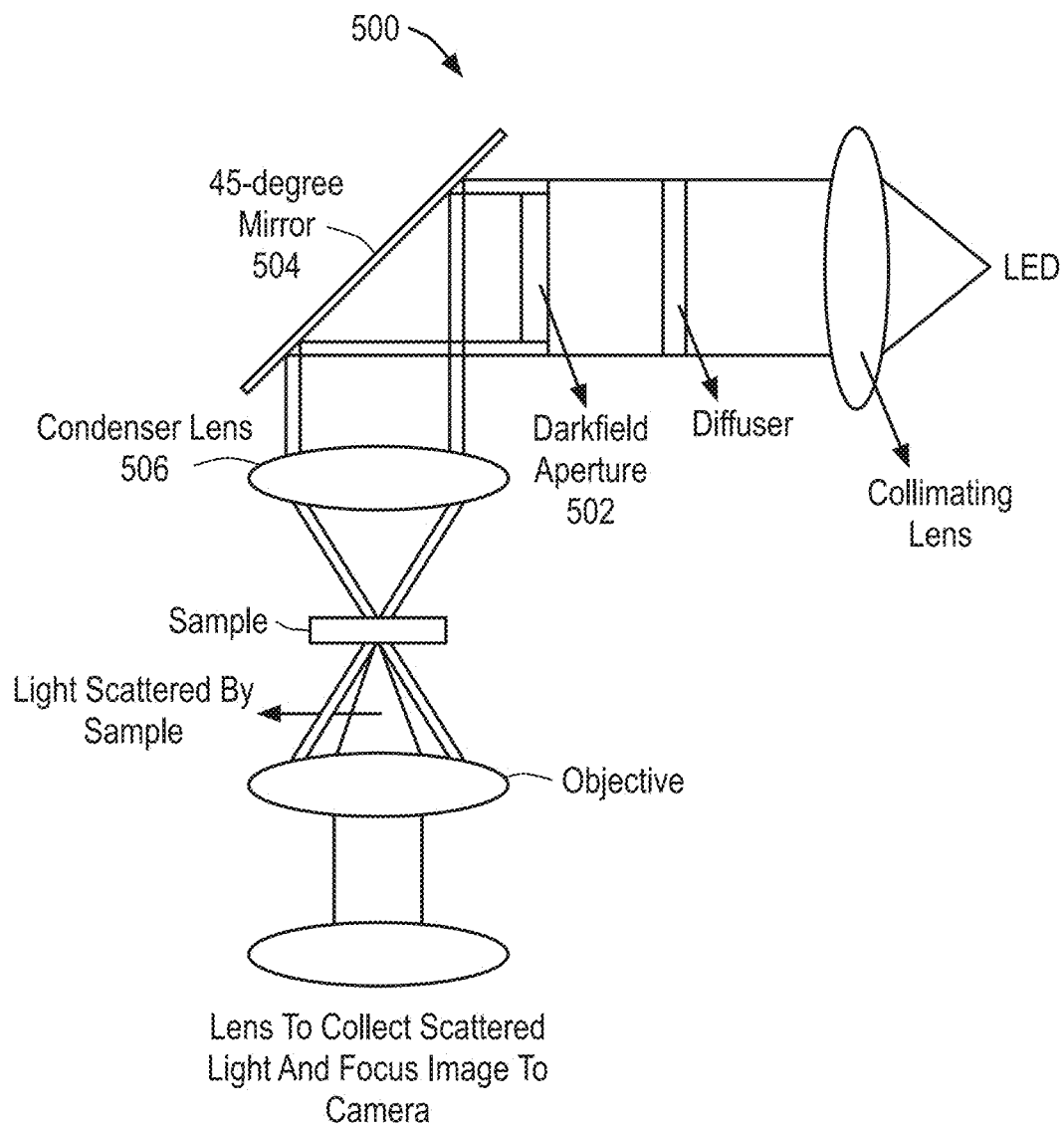
FIG. 14A-C illustrate schematic views of examples of darkfield illumination systems that may be used by microscope 4, according to an embodiment of the invention.
Figure 14B:
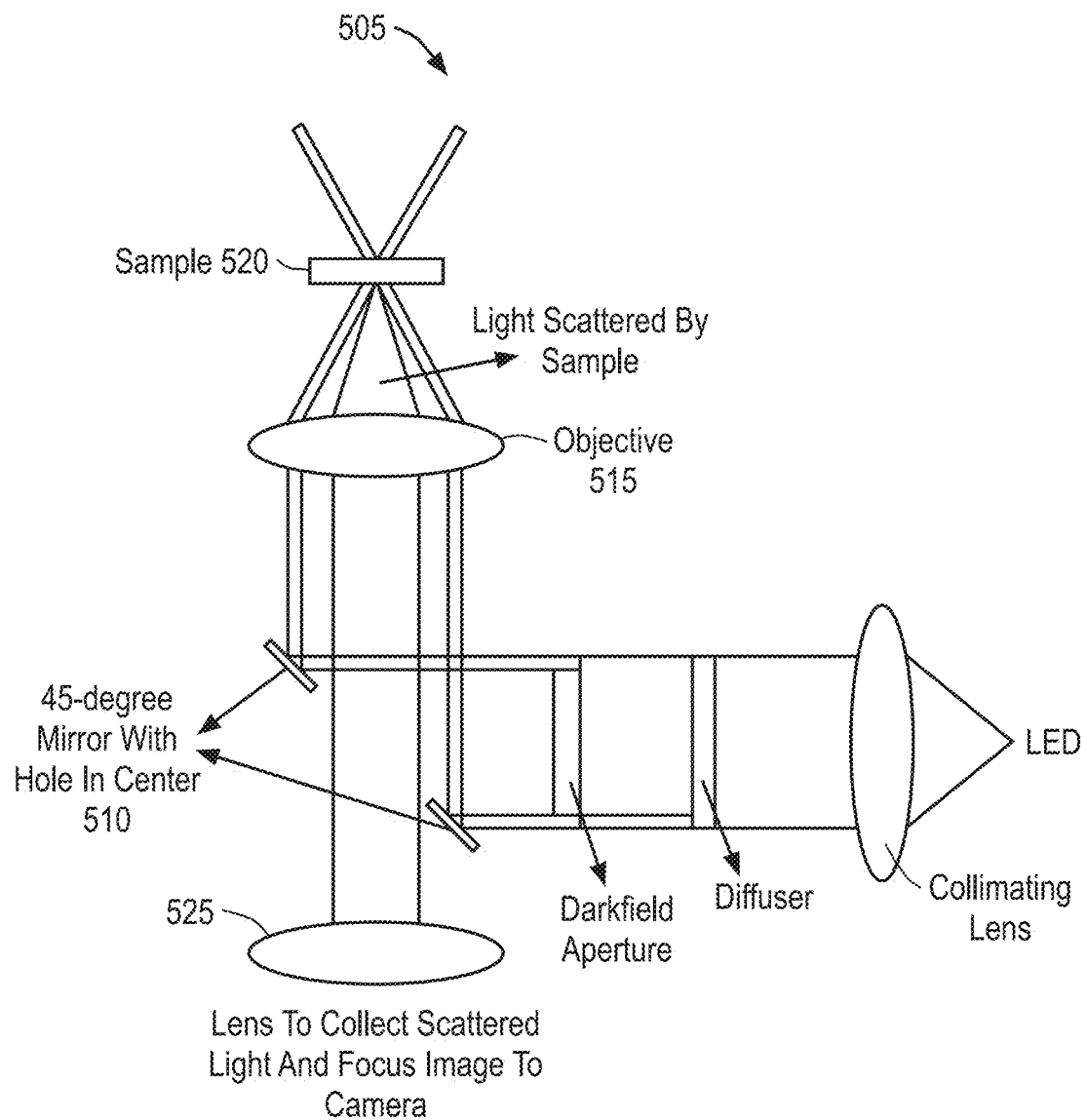
Figure 14C:
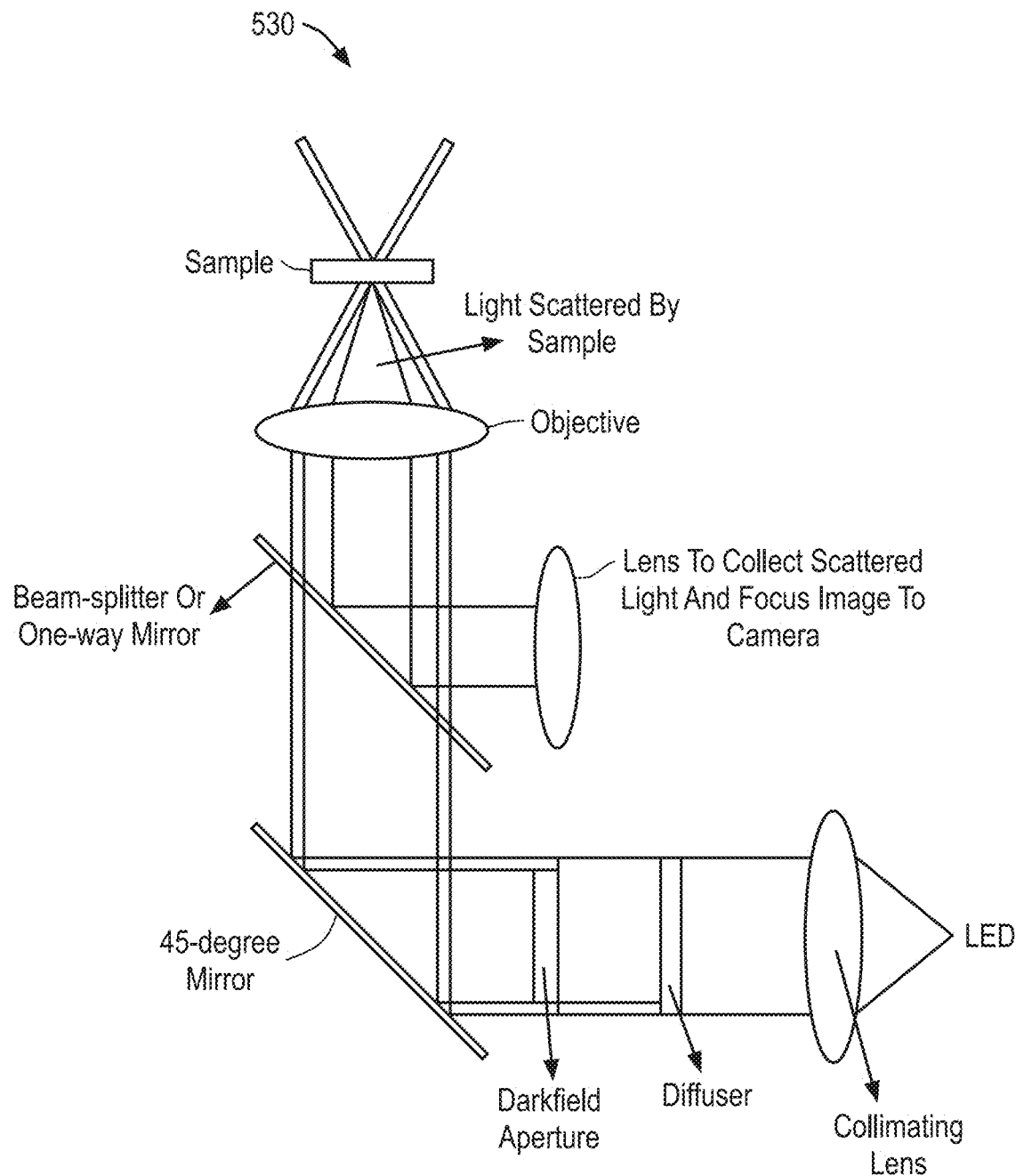

The imaging system for time-lapse imaging may employ brightfield illumination, darkfield illumination, phase contrast, Hoffman modulation contrast, differential interference contrast, polarized light, fluorescence, single or multiplane or combinations thereof. In some embodiments, darkfield illumination may be used to provide enhanced image contrast for subsequent feature extraction and image analysis. In addition, red or near-infrared light sources may be used to reduce phototoxicity and improve the contrast ratio between cell membranes and the inner portion of the cells. FIG. 14A-C illustrates a schematic view of darkfield illumination systems that may be used by the microscope. Darkfield illumination system 500 of FIG. 14A illustrates an example of a traditional darkfield illumination approach for use with time-lapse microscopes such as the microscope 400, darkfield illumination system 505 of FIG. 14B illustrates an example of an approach using epi-illumination, and darkfield illumination system 530 of FIG. 14C illustrates another approach for epi-illuminated darkfield. In system 505, for example, a 45-degree mirror 510 with a circular hole in the middle can be placed under the imaging objective 515. A hollow cone of light is reflected off the mirror and up towards the imaging objective 515, where it gets focused to the sample 520. Light scattered by the sample 520 gets collected by the same imaging objective 515 and passes through the hole in the mirror 510 and towards a tube-lens and camera 525 for collecting the image. In addition, red or near-infrared light sources may be used to reduce phototoxicity and improve the contrast ratio between cell membranes and the inner portion of the cells. In other embodiments, images can be captured using one or more illumination wavelengths and the various images can be combined or used to provide additional information.

In one embodiment, a darkfield aperture 502 illustrated in FIG. 14A may be placed as shown. Alternatively, the darkfield aperture 502 may be placed in other configurations, such as between the 45-degree mirror 504 and the condenser lens 506, or after the condenser lens 506.

Images that are acquired may be stored either on a continuous basis, as in live video, or on an intermittent basis, as in time lapse photography, where a subject is repeatedly imaged in a still picture. Images may also be acquired in response to a detected event or a scheduled event in order to, for example, obtain a more granular image based features from increased or decreased sampling of an image sequence. Preferably, the time interval between images should be between 1 to 30 minutes, or between 1 to 20 minutes or between 1 to 15 minutes, or between 1 to 10 minutes or between 1 to 5 minutes in order to capture significant morphological events as described below. In an alternative embodiment, the time interval between images could be varied depending on the amount of cell activity. For example, during active periods images could be taken as often as every few seconds or every minute, while during inactive periods images could be taken every 10 or 15 minutes or longer. Real-time image analysis on the captured images could be used to detect when and how to vary the time intervals. In our methods, the total amount of light received by the samples is estimated to be equivalent to approximately 52 seconds of continuous low-level light exposure for 5-days of imaging. The light intensity for a time-lapse imaging system is significantly lower than the light intensity typically used on an assisted reproduction microscope due to the low-power of the LEDs (for example, using a 1 W LED compared to a typical 100 W Halogen bulb) and high sensitivity of the camera sensor. Thus, the total amount of light energy received by an embryo using the time-lapse imaging system is comparable to or less than the amount of energy received during routine handling at an IVF clinic. In addition, exposure time can be significantly shortened to reduce the total amount of light exposure to the embryo. For 2-days of imaging, with images captured every 5 minutes at 0.5 seconds of light exposure per image, the total amount of low-level light exposure is less than 21 seconds. A camera system suitable for capturing images is described in U.S. Pat. No. 8,265,357. In this system, the time-lapse recording of the embryos is directed by an image analysis software that controls the movements of the scanning stage holding the microscope slide; the operation a highly light sensitive video camera; and the storage and recording of time lapse sequences on a computer hard disk.

Following image acquisition, the embryos are localized and analyzed for different cellular parameters or image based parameters, for example, zygote size, blastomere size, thickness of the zona pellucida, smoothness or ruffling of the plasma membrane, smoothness or ruffling of the oolemma, formation of one or more pseudo cleavage furrows, degree of fragmentation, symmetry of daughter cells resulting from a cell division, time intervals between the first few mitoses, duration of cytokinesis, timing and quality of syngamy, area of outer boundary segmentation, boundary segment distribution at the center of the embryo, changes in standard deviation of segment distribution at the center of the embryo, embryo shape, and texture at the edge or center of the embryo. Image analysis methods that may be used to analyze cellular and image based parameters include, for example, shape based methods (e.g., thresholding, blob extraction, template matching and Hough transforms (lines, ellipses, arbitrary shape, etc.)), low level methods (e.g., detecting edges, texture, ridges, corners, blobs; local image feature detectors such as scale-invariant feature transform (SIFT) and speeded up robust features (SURF), local binary patterns (LBP), SIFT-like GLOH features, PCA-SIFT, and SIFT-Rank detector), and curvature methods (e.g., edge direction, changing intensity, and correlation). Additional cellular and image-based parameters that can be analyzed are described in WO 2014/001312 and WO 2014/033210. Analysis can involve measuring features, e.g., texture, for the entire embryo, or at specific regions of the embryo such as the embryo edge and/or at the embryo center. These cellular or image based parameters may be used in conjunction with classifiers, cluster methods and like to produce the intended prediction of clinical variables Cellular parameters that may be measured by time-lapse imaging are usually morphological events. For example, in assessing embryos, time-lapse imaging may be used to visualize the duration of compaction and/or cavitation and/or expansion and/or collapse. Additionally, time-lapse imaging may be used to measure the duration of time between compaction and the onset or resolution of cavitation, expansion, or collapse or the time from first cleavage to cavitation (tCav) Additionally, time-lapse imaging may be used to measure the duration of time between cavitation and the onset or resolution of expansion or collapse. Time-lapse imaging may be used to measure the time between the onset of expansion and the onset or resolution of collapse. Another parameter of interest is the frequency of blastocyst expansion and/or collapse. Other parameters of interest are the rate of expansion, the rate of collapse, average embryo size after initial expansion (Pexp-area), the degree of expansion and the degree of collapse. Cellular parameters of interest that can be measured by time-lapse imaging include time intervals that are defined by these cellular events, e.g. (a) the time interval between compaction and cavitation, definable as any one of the interval between initiation of compaction and the initiation of cavitation, the interval between the resolution of compaction and the resolution of cavitation, the interval between the initiation of compaction and the resolution of cavitation; or the interval between the resolution of compaction and the initiation of cavitation; or (b) the time interval between cavitation and expansion, definable as any one of the interval between the initiation of cavitation and the initiation of expansion, or the interval between resolution of the cavitation and the resolution of expansion, or the interval between initiation of cavitation and the resolution of expansion, or the interval between resolution of cavitation and the initiation of expansion; or (c) the time interval between expansion and collapse, definable as any one of the interval between initiation of expansion and the initiation of collapse, the interval between the resolution of expansion and the resolution of collapse, the interval between the initiation of expansion and the resolution of collapse; or the interval between the resolution of expansion and the initiation of collapse. Volume or size may be estimated or determined by measuring, for example, the diameter and/or circumference and/or area of the blastocyst. For example, time lapse microscopy image parameters, such as embryo outer boundary segmentation, can be used to calculate the area of the embryo described herein.

For the purposes of in vitro fertilization, it is considered advantageous that the embryo be transferred to the uterus early in development to reduce embryo loss due to disadvantages of culture conditions relative to the in vitro environment, and to reduce potential adverse outcomes associated with epigenetic errors that may occur during culturing (Katari et al. (2009) Hum Mol Genet. 18(20):3769-78; Sepulveda et al. (2009) Fertil Steril. 91(5):1765-70). Accordingly, it is preferable that the measurement of compaction and/or cavitation and/or expansion and/or collapse parameters take place within about 36 hours, about 54 hours, about 60 hours, about 72 hours, about 84 hours, about 96 hours, about 120 hours, or more. Morula and blastocyst formation generally occur at about day 3 to day 5 following fertilization, and, therefore, certain parameters, e.g., blastocyst expansion and collapse, may require in vitro culture of the embryo for up to about 5 days or longer.

Parameters can be measured manually, or they may be measured automatically, e.g. by image analysis software. When image analysis software is employed, image analysis algorithms may be used that employ a probabilistic model estimation technique. The probabilistic model estimation technique may be based on a sequential Monte Carlo method, e.g. generating distributions of hypothesized embryo models, simulating images based on a simple optical model, and comparing these simulations to the observed image data. When such probabilistic model estimations are employed, cells may be modeled as any appropriate shape, e.g. as collections of ellipses in 2D space, collections of ellipsoids in 3D space, and the like. To deal with occlusions and depth ambiguities, the method can enforce geometrical constraints that correspond to expected physical behavior. To improve robustness, images can be captured at one or more focal planes. A more detailed description of such a technique is provided in U.S. Pat. No. 7,963,906. Alternatively or in addition, the image analysis algorithm may leverage observable cell features such as boundary segments in a conditional random field (CRF) model over which multi-pass data driven approximate inference may be performed. A more detailed description of such a technique is provided in Moussavi, et al. (2014) "A Unified Graphical Models Framework for Automated Human Embryo Tracking in Time Lapse Microscopy," International Symposium on Biomedical Imaging, In Press. Methods other than probabilistic models may also be employed that do not track cells individually but extract features directly from the images and use those features for classification or analysis. For example, image-based cell classification and/or outcome-based classification applied to series of images may be employed. The classification may be based on features including handcrafted and/or machine learned features. A more detailed description of such a classification approach is provided in *Automated embryo stage classification in time-lapse microscopy video of early human embryo development*, Yu Wang, Farshid Moussavi, Peter Lorenzen, International Conference on Medical Image Computing and Computer Assisted Intervention (MICCAI), vol. 8150 of Lecture Notes in Computer Science, pages 460-467, Springer, 2013. Classification-based approaches may also be used in conjunction with tracking-based approaches, as described in Moussavi, et al. (2014) "A Unified Graphical Models Framework for Automated Human Embryo Tracking in Time Lapse Microscopy," International Symposium on Biomedical Imaging, In Press. Other algorithms and methods for analyzing images are described in U.S. Pat. No. 8,265,357, WO 2014/001312 and WO 2014/033210.

Once cell parameter measurements have been obtained, the measurements are employed to determine the likelihood that the embryo will develop into a blastocyst and/or become a good quality blastocyst and/or implant into the uterus and/or be born live and/or be euploid. For example, a compaction and/or cavitation and/or expansion and/or collapse parameter may be used to determine the likelihood that the embryo is euploid. Alternatively, a compaction and/or cavitation and/or expansion and/or collapse parameter may be used to determine the likelihood that the embryo is aneuploid.

Alternatively, the measurements can be employed to make patient treatment outcome predictions including the likelihood that a patient received one or more of said embryos will become pregnant and/or will carry the pregnancy to term or miscarry. The measurements may also be used to determine the likelihood that a particular female will produce at least one euploid blastocyst.

In some embodiments, the compaction and/or cavitation parameter measurement is used directly to determine the likelihood that an embryo will be euploid, will reach the blastocyst stage or will become a good quality embryo. In some embodiments, the compaction and/or cavitation and/or expansion and/or collapse parameter measurement is used directly to determine the likelihood that an embryo will be euploid and/or successfully implant into the uterus and/or will be born live. In other words, the absolute value of the measurement itself is sufficient to determine the likelihood that an embryo will be euploid and/or reach the blastocyst stage and/or implant into the uterus and/or be born live.

In some embodiments, the compaction and/or cavitation and/or expansion and/or collapse parameter measurement is employed by comparing it to a respective compaction and/or cavitation and/or expansion and/or collapse parameter measurement from a reference, or control, embryo, and using the result of this comparison to provide a determination of the likelihood of the embryo to be euploid, to reach or not reach the blastocyst stage, and/or become a good quality blastocyst and/or implant into the uterus and/or be born live. The terms "reference" and "control" as used herein mean a standardized embryo or cell to be used to interpret the compaction and/or cavitation and/or expansion and/or collapse parameter measurements of a given embryo and assign a determination of the likelihood of the embryo to be euploid, to reach the blastocyst stage, and/or become a good quality blastocyst and/or implant into the uterus and/or be born live. The reference or control may be an embryo that is known to have a desired phenotype, e.g., euploid, likely to reach the blastocyst stage, and/or become a good quality blastocyst and/or implant into the uterus and/or be born live, and therefore may be a positive reference or control embryo. Alternatively, the reference/control embryo may be an embryo known to not have the desired phenotype, e.g., an aneuploid embryo, and therefore be a negative reference/control embryo.

In certain embodiments, compaction and/or cavitation and/or expansion and/or collapse parameters are first employed to determine whether an embryo will be euploid, likely to reach the blastocyst stage, and/or become a good quality blastocyst and/or implant into a uterus and/or be born live. In such embodiments, embryos that fall within one or more of the above referenced compaction and/or cavitation and/or expansion and/or collapse parameter time frames (e.g. duration of compaction, duration of cavitation, duration of expansion, duration of collapse, duration between compaction and cavitation, duration between cavitation and expansion, and/or duration between expansion an collapse) is selected to have good developmental potential. These embryos are then analyzed to determine if they have a normal compaction and/or cavitation and/or expansion and/or collapse duration and/or duration of interval between compaction and/or cavitation and/or expansion and/or collapse. Embryos previously selected to have good developmental potential are deselected when they are determined to have prolonged or shortened compaction and/or cavitation and/or expansion and/or collapse duration and/or one or more abnormal duration of intervals between compaction and/or cavitation and/or expansion and/or collapse, thereby selecting for implantation or freezing for potential future implantation, only those embryos that fall within the selection criteria and outside the deselection criteria.

In certain embodiments, the obtained compaction and/or cavitation and/or expansion and/or collapse parameter measurement(s) is compared to a comparable compaction and/or cavitation and/or expansion and/or collapse parameter measurement(s) from a single reference/control embryo to obtain information regarding the phenotype of the embryo/cell being assayed. In yet other embodiments, the obtained compaction and/or cavitation and/or expansion and/or collapse parameter measurement(s) is compared to the comparable compaction and/or cavitation and/or expansion and/or collapse parameter measurement(s) from two or more different reference/control embryos to obtain more in depth information regarding the phenotype of the assayed embryo/cell. For example, the obtained compaction and/or cavitation and/or expansion and/or collapse parameter measurements from the embryo(s) being assessed may be compared to both a positive and negative embryo to obtain confirmed information regarding whether the embryo/cell has the phenotype of interest.

As discussed above, one or more parameters may be measured and employed to determine the likelihood of being euploid, reaching the blastocyst stage and/or becoming a good quality blastocyst and/or implant into the uterus and/or be born live for an embryo. In some embodiments, a measurement of two parameters may be sufficient to arrive at a determination of the likelihood of being euploid, reaching the blastocyst stage and/or becoming a good quality blastocyst and/or implant into the uterus and/or be born live. In some embodiments, it may be desirable to employ measurements of more than two parameters, for example, 3 cellular parameters or 4 or more cellular parameters. In some embodiments, it may be desirable to measure one or more parameters for selecting an embryo with good developmental potential and one or more parameters for deselecting embryos with poor developmental potential. In certain embodiments, 1 selection parameter and 1 deselection parameter is measured. In another embodiment, 1 selection parameter and 2 deselection parameters are measured. In another embodiment, 1 selection parameter and 3 deselection parameters are measured. In another embodiment, 2 selection parameters and 1 deselection parameter are measured. In another embodiment, 3 selection parameter and 1 deselection parameter are measured. In another embodiment, more than 3 selection parameters and 1 deselection parameter are measured. In another embodiment, 2 selection parameters and 2 deselection parameters are measured. In another embodiment, 2 selection parameters and 3 deselection parameters are measured. In another embodiment, 3 selection parameters and 2 deselection parameters are measured. In another embodiment, more than 3 selection parameters and 2 deselection parameters are measured. In another embodiment, more than 3 selection parameters and 3 deselection parameters are measured.

In some embodiments, Age may be combined with one or more other parameters listed in Tables 1 and 2 to determine the likelihood that an embryo will be aneuploid or euploid. In one embodiment age is combined in a single classifier with #2PN, tCav and Psyn. In another embodiment, Age is combined in a single classifier with Pexp-area, and P3. In some embodiments, the classifier is used to categorize the embryos in grades or rankings from 1-5 to determine the relative likelihood of aneuploidy in an embryo. Classifier methods and algorithms described in U.S. patent application Ser. No. 14/194,386, hereby incorporated by reference in its entirety may be used to combine analyze the parameters and categorize embryos.

In some embodiments, the cellular parameters described herein may be used to determine the likelihood that an embryo will implant into the uterus of a female. In such embodiments, embryos that have first been determined to be euploid either by PGS or by the methods described herein (or both) are further analyzed to determine the percentage of time the embryo spends expanding or put another way, the average amount of time an embryo spends in expansion. In such embodiments, an embryo that spends a longer period of time in expansion relative to another embryo is more likely to implant than the embryo that spends a shorter period of time in expansion. In this embodiment, embryos may be ranked relative to each other based on the percentage of time each spends in expansion. In another embodiment, the percentage of time itself may be used as a metric for the likelihood that a euploid embryo will implant into the uterus. In such embodiments, an embryo that spends at least about 85% of the time in expansion has a greater likelihood of implanting than an embryo that spends less than about 85% of the time expanding. Furthermore, an embryo that spends at least 86%, 87%, 88%, 89% or 90% or greater in expansion has a high likelihood of implantation. Conversely, a euploid embryo that spends less than about 85% of the time expanding has a decreased likelihood that it will implant into the uterus.

In some embodiments, the average amount of time that a euploid embryo spends in each expansion event is predictive of whether or not the euploid embryo will implant into the uterus. In this embodiment, the longer than a euploid embryo spends in each expansion event relative to another embryo is indicative of a greater likelihood that the euploid embryo will implant into the uterus. In another embodiment, the average time spent in each expansion event itself may be used as a metric for the likelihood that a euploid embryo will implant into the uterus. In such embodiments, an embryo that spends at least about an average of 120 minutes or longer in each expansion event has a greater likelihood of implantation than an embryo that spends less than about 120 minutes in each expansion event. Furthermore, an embryo that spends an average of at least about 125, 130, or 135 minutes or longer in each expansion event has a greater likelihood of implantation. Conversely, a euploid embryo that spends less than an average of about 120 minutes or 115 minutes in each expansion has a lower likelihood of implantation.

In certain embodiments, assaying for multiple parameters may be desirable as assaying for multiple parameters may provide for greater sensitivity and specificity. By sensitivity it is meant the proportion of actual positives which are correctly identified as being such. This may be depicted mathematically as:

$$\text{Sensitivity} = \frac{\text{(Number of true positives)}}{\text{(Number of true positives + Number of false negatives)}}$$

Thus, in a method in which "positives" are the embryos that have good developmental potential, i.e. that will become a good quality blastocyst and/or implant into the uterus and/or euploid, and "negatives" are the embryos that have poor developmental potential, i.e. that will not develop into good quality blastocysts and/or implant into the uterus and/or will be euploid, a sensitivity of 100% means that the test recognizes all embryos that will become good quality blastocysts or implant in to the uterus or be chromosomally normal as such. In some embodiments, the sensitivity of the assay may be about 70%, 80%, 90%, 95%, 98% or more, e.g. 100%. By specificity it is meant the proportion of "negatives" which are correctly identified as such. As discussed above, the term "specificity" when used herein with respect to prediction and/or evaluation methods is used to refer to the ability to predict or evaluate an embryo for determining the likelihood that the embryo will not become a good quality blastocyst or implant into the uterus or be euploid by assessing, determining, identifying or selecting embryos that are not likely to become a good quality blastocyst and/or implant into the uterus and/or be euploid. This may be depicted mathematically as:

$$\text{Specificity} = \frac{\text{(Number of true negatives)}}{\text{(Number of true negatives + Number of false positives)}}$$

Thus, in a method in which positives are the embryos that are likely to become good quality blastocysts and/or implant into the uterus and/or be euploid, and negatives are the embryos that are likely not to develop into good quality blastocysts and/or implant into the uterus and/or be euploid, a specificity of 100% means that the test recognizes all embryos that will not develop into good quality blastocysts and/or implant into the uterus and/or be euploid. In some embodiments, the specificity can be a "high specificity." In addition, the specified mean values and/or cut-off points may be modified depending upon the data set used to calculate these values as well as the specific application. Identification embryos that are likely to become good quality blastocysts and/or implant into the uterus and/or be euploid can be done by using classification software such as is described in U.S. patent application Ser. No. 14/194,386, which is incorporated by reference in its entirety.

In some embodiments, the assessment of an embryo includes generating a written report that includes the artisan's assessment of the subject embryo, e.g. "assessment/selection/determination of embryos likely and/or not likely to develop into good quality blastocysts and/or implant into the uterus", an "assessment of chromosomal abnormalities", etc. Thus, a subject method may further include a step of generating or outputting a report providing the results of such an assessment, which report can be provided in the form of an electronic medium (e.g., an electronic display on a computer monitor), or in the form of a tangible medium (e.g., a report printed on paper or other tangible medium).

A "report," as described herein, is an electronic or tangible document which includes report elements that provide information of interest relating to an assessment arrived at by methods of the invention. A subject report can be completely or partially electronically generated. A subject report includes at least an assessment of the likelihood of the subject embryo or to reach the blastocyst stage and/or implant into the uterus, an assessment of the probability of the existence of chromosomal abnormalities, etc. A subject report can further include one or more of: 1) information regarding the testing facility; 2) service provider information; 3) subject data; 4) sample data; 5) a detailed assessment report section, providing information relating to how the assessment was arrived at, e.g. a) cell parameter measurements taken, b) reference values employed, if any; and 6) other features.

The report may include information about the testing facility, which information is relevant to the hospital, clinic, or laboratory in which sample gathering and/or data generation was conducted. Sample gathering can include how the sample was generated, e.g. how it was harvested from a subject, and/or how it was cultured etc. Data generation can include how images were acquired or gene expression profiles were analyzed. This information can include one or more details relating to, for example, the name and location of the testing facility, the identity of the lab technician who conducted the assay and/or who entered the input data, the date and time the assay was conducted and/or analyzed, the location where the sample and/or result data is stored, the lot number of the reagents or culture media (e.g., kit, etc.) used in the assay, and the like. Report fields with this information can generally be populated using information provided by the user.

The report may include information about the service provider, which may be located outside the healthcare facility at which the user is located, or within the healthcare facility. Examples of such information can include the name and location of the service provider, the name of the reviewer, and where necessary or desired the name of the individual who conducted sample preparation and/or data generation. Report fields with this information can generally be populated using data entered by the user, which can be selected from among pre-scripted selections (e.g., using a drop-down menu). Other service provider information in the report can include contact information for technical information about the result and/or about the interpretive report.

The report may include a subject data section, including medical history of subjects from which oocytes or were harvested, patient age, in vitro fertilization cycle characteristics (e.g. fertilization rate, day 3 follicle stimulating hormone (FSH) level), and, when oocytes are harvested, zygote/embryo cohort parameters (e.g. total number of embryos). This subject data may be integrated to improve embryo assessment and/or help determine the optimal number of embryos to transfer. The report may also include administrative subject data (that is, data that are not essential to the assessment of the likelihood of implanting into the uterus) such as information to identify the subject (e.g., name, subject date of birth (DOB), gender, mailing and/or residence address, medical record number (MRN), room and/or bed number in a healthcare facility), insurance information, and the like), the name of the subject's physician or other health professional who ordered the assessment of developmental potential and, if different from the ordering physician, the name of a staff physician who is responsible for the subject's care (e.g., primary care physician).

The report may include a sample data section, which may provide information about the biological sample analyzed in the assessment, such as how the sample was handled (e.g. storage temperature, preparatory protocols) and the date and time collected. Report fields with this information can generally be populated using data entered by the user, some of which may be provided as pre-scripted selections (e.g., using a drop-down menu).

The report may include an assessment report section, which may include information relating to how the assessments/determinations were arrived at as described herein. The interpretive report can include, for example, time-lapse images of the embryo or being assessed, and/or gene expression results. The assessment portion of the report can optionally also include a recommendation(s) section. For example, where the results indicate that the embryo is likely to reach the blastocyst stage and/or implant into the uterus, the recommendation can include a recommendation that a limited number of embryos be transplanted into the uterus during fertility treatment as recommended in the art.

It will also be readily appreciated that the reports can include additional elements or modified elements. For example, where electronic, the report can contain hyperlinks which point to internal or external databases which provide more detailed information about selected elements of the report. For example, the patient data element of the report can include a hyperlink to an electronic patient record, or a site for accessing such a patient record, which patient record is maintained in a confidential database. This latter embodiment may be of interest in an in-hospital system or in-clinic setting. When in electronic format, the report is recorded on a suitable physical medium, such as a computer readable medium, e.g., in a computer memory, zip drive, CD, DVD, etc.

It will be readily appreciated that the report can include all or some of the elements above, with the proviso that the report generally includes at least the elements sufficient to provide the analysis requested by the user (e.g., an assessment of the likelihood of reaching the blastocyst stage, and/or develop into good quality blastocysts and/or implant into the uterus).

As discussed above, methods of the invention may be used to assess embryos or cells to determine the likelihood of the embryos to be euploid, reach the blastocyst stage, and/or develop into good quality blastocysts and/or implant into the uterus and or be born live. This determination of the likelihood of the embryos to be euploid, to reach the blastocyst stage and/or implant into the uterus and/or be born live may be used to guide clinical decisions and/or actions. For example, in order to increase pregnancy rates, clinicians often transfer multiple embryos into patients, potentially resulting in multiple pregnancies that pose health risks to both the mother and fetuses. Using results obtained from the methods of the invention, the likelihood of reaching the blastocyst stage, and/or developing into good quality blastocysts and/or implanting into the uterus and/or be born live can be determined for embryos being transferred. As the embryos that are likely to be euploid, reach the blastocyst stage, and/or develop into good quality blastocysts and/or implant into the uterus and/or be born live are more likely to develop into fetuses, the determination of the likelihood of the embryo to be euploid, reach the blastocyst stage, and/or develop into good quality blastocysts and/or implant into the uterus and/or be born live prior to transplantation allows the practitioner to decide how many embryos to transfer so as to maximize the chance of success of a full term pregnancy while minimizing risk.

Assessments made by following methods of the invention may also find use in ranking embryos in a group of embryos for the likelihood that the embryos will be euploid, will reach the blastocyst stage as well as for the quality of the blastocyst that will be achieved (e.g., in some embodiments this would include the likelihood of implanting into the uterus and/or being chromosomally normal). For example, in some instances, multiple embryos may be euploid and/or capable of developing into blastocysts, i.e. multiple embryos are likely to reach the blastocyst stage. However, some embryos will be more likely to be euploid and/or achieve the blastocyst stage, i.e. they will have better likelihood to reach the blastocyst stage, or better likelihood to develop into good quality blastocyst, or better likelihood to implant into the uterus than other embryos. In such cases, methods of the invention may be used to rank the embryos in the group. In such methods, one or more cellular parameters for each embryo is measured to arrive at a cell parameter measurement for each embryo. The one or more cell parameter measurements from each of the embryos are then employed to determine the likelihood of the embryos relative to one another to be euploid, reach the blastocyst stage and/or to implant into the uterus and/or be born live. In some embodiments, the cell parameter measurements from each of the embryos or are employed by comparing them directly to one another to determine the likelihood of being euploid, reaching the blastocyst stage and/or implant into the uterus and/or be born live. In some embodiments, the cell parameter measurements from each of the embryos are employed by comparing the cell parameter measurements to a cell parameter measurement from a reference embryo to determine likelihood of being euploid, reaching the blastocyst stage, implant into the uterus and/or be born live for each embryo, and then comparing the determination of the likelihood of being euploid, reaching the blastocyst stage, implant into the uterus and/or be born live for each embryo to determine the likelihood of reaching the blastocyst stage, implant into the uterus and/or be born live of the embryos or relative to one another.

In this way, a practitioner assessing, for example, multiple zygotes/embryos, can choose only the best quality embryos, i.e. those with the best likelihood of implanting into the uterus and/or being euploid to transfer so as to maximize the chance of success of a full term pregnancy while minimizing risk.

Also provided are reagents, devices and kits thereof for practicing one or more of the above-described methods. The subject reagents, devices and kits thereof may vary greatly. Reagents and devices of interest include those mentioned above with respect to the methods of measuring any of the aforementioned cellular parameters, where such reagents may include culture plates, culture media, microscopes, imaging software, imaging analysis software, nucleic acid primers, arrays of nucleic acid probes, antibodies, signal producing system reagents, etc., depending on the particular measuring protocol to be performed.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc.

Yet another means would be a computer readable medium, e.g., diskette, CD, etc., on which the information has been recorded. Yet another means that may be present is a website address which may be used via the internet to access the information at a removed site. Any convenient means may be present in the kits.

Some of the methods described above require the ability to observe embryo development via time-lapse imaging. This can be achieved using a system comprised of a miniature, multi-channel microscope array that can fit inside a standard incubator. This allows multiple samples to be imaged quickly and simultaneously without having to physically move the dishes. One illustrative prototype, shown in FIG. 22 of U.S. Pat. No. 7,963,906, consists of a 3-channel microscope array with darkfield illumination, although other types of illumination could be used. By "three channel," it is meant that there are three independent microscopes imaging three distinct culture dishes simultaneously. A stepper motor is used to adjust the focal position for focusing or acquiring 3D image stacks. White-light LEDs are used for illumination, although we have observed that for human embryos, using red or near-infrared (IR) LEDs can improve the contrast ratio between cell membranes and the inner portions of the cells. This improved contrast ratio can help with both manual and automated image analysis. In addition, moving to the infrared region can reduce phototoxicity to the samples. Images are captured by low-cost, high-resolution webcams, but other types of cameras may be used.

As shown in FIG. 22 of U.S. Pat. No. 7,963,906, each microscope of the prototype system described above is used to image a culture dish which may contain anywhere from 1-30 embryos. The microscope collects light from a white light LED connected to a heat sink to help dissipate any heat generated by the LED, which is very small for brief exposure times. The light passes through a conventional dark field patch for stopping direct light, through a condenser lens and onto a specimen labeled "petri dish," which is a culture dish holding the embryos being cultured and studied. The culture dish may have wells that help maintain the order of the embryos and keep them from moving while the dish is being carried to and from the incubator. The wells can be spaced close enough together so that embryos can share the same media drop. The scattered light is then passed through a microscope objective, then through an achromat doublet, and onto a CMOS sensor. The CMOS sensor acts as a digital camera and is connected to a computer for image analysis and tracking as described above.

This design is easily scalable to provide significantly more channels and different illumination techniques, and can be modified to accommodate fluidic devices for feeding the samples. In addition, the design can be integrated with a feedback control system, where culture conditions such as temperature, CO2 (to control pH), and media are optimized in real-time based on feedback and from the imaging data. This system was used to acquire time-lapse videos of human embryo development, which has utility in determining embryo viability for in vitro fertilization (IVF) procedures. Other applications include stem cell therapy, drug screening, and tissue engineering.

In one embodiment of the device, illumination is provided by a Luxeon white light-emitting diode (LED) mounted on an aluminum heat sink and powered by a BuckPuck current regulated driver. Light from the LED is passed through a collimating lens. The collimated light then passes through a custom laser-machined patch stop, as shown in FIG. 22 of U.S. Pat. No. 7,963,906, and focused into a hollow cone of light using an aspheric condenser lens. Light that is directly transmitted through the sample is rejected by the objective, while light that is scattered by the sample is collected. In one embodiment, Olympus objectives with 20× magnification are used, although smaller magnifications can be used to increase the field-of-view, or larger magnifications can be used to increase resolution. The collected light is then passed through an achromat doublet lens (i.e. tube lens) to reduce the effects of chromatic and spherical aberration. Alternatively, the collected light from the imaging objective can be passed through another objective, pointed in the opposing direction that acts as a replacement to the tube lens. In one configuration, the imaging objective can be a 10× objective, while the tube-lens objective can be a 4× objective. The resulting image is captured by a CMOS sensor with 2 megapixel resolution (1600×1200 pixels). Different types of sensors and resolutions can also be used.

For example, FIG. 23A of U.S. Pat. No. 7,963,906 shows a schematic of the multi-channel microscope array having 3 identical microscopes. All optical components are mounted in lens tubes. In operation of the array system, Petri dishes are loaded on acrylic platforms that are mounted on manual 2-axis tilt stages, which allow adjustment of the image plane relative to the optical axis. These stages are fixed to the base of the microscope and do not move after the initial alignment. The illumination modules, consisting of the LEDs, collimator lenses, patch stops, and condenser lenses, are mounted on manual xyz stages for positioning and focusing the illumination light. The imaging modules, consisting of the objectives, achromat lenses, and CMOS sensors, are also mounted on manual xyz stages for positioning the field-of-view and focusing the objectives. All 3 of the imaging modules are attached to linear slides and supported by a single lever arm, which is actuated using a stepper motor. This allows for computer-controlled focusing and automatic capture of image-stacks. Other methods of automatic focusing as well as actuation can be used.

The microscope array was placed inside a standard incubator, as shown in, for example, FIG. 23B of U.S. Pat. No. 7,963,906. The CMOS image sensors are connected via USB connection to a single hub located inside the incubator, which is routed to an external PC along with other communication and power lines. All electrical cables exit the incubator through the center of a rubber stopper sealed with silicone glue.

The above described microscope array, or one similar, can be used to record time-lapse images of early human embryo development and documented growth from zygote through blastocyst stages. In some embodiments, images can be captured every 5 minutes with roughly 1 second of low-light exposure per image. The total amount of light received by the samples can be equivalent to 52 seconds of continuous exposure, similar to the total level experienced in an IVF clinic during handling. The 1 second duration of light exposure per image can in some embodiments be reduced. Prior to working with the human embryos, extensive control experiments were performed with mouse pre-implantation embryos to ensure that both the blastocyst formation rate and gene expression patterns were not affected by the imaging process.

Individual embryos can be followed over time, even though their positions in the photographic field shifted as the embryos underwent a media change, in some cases the media was changed at day 3. The use of sequential media may be needed to meet the stage-specific requirements of the developing embryos. During media change, the embryos were removed from the imaging station for a few minutes and transferred to new petri dishes. The issue of tracking embryo identity can be mitigated by using wells to help arrange the embryos in a particular order.

When transferring the petri dishes between different stations, the embryos can sometimes move around, thereby making it difficult to keep track of embryo identity. This poses a challenge when time-lapse imaging is performed on one station, and the embryos are subsequently moved to a second station for embryo selection and transfer. One method is to culture embryos in individual petri dishes. However, this requires each embryo to have its own media drop. In a typical IVF procedure, it is usually desirable to culture all of a patient's embryos on the same petri dish and in the same media drop. To address this problem, we have designed a custom petri dish with micro-wells. This keeps the embryos from moving around and maintains their arrangement on the petri dish when transferred to and from the incubator or imaging stations. In addition, the wells are small enough and spaced closely together such that they can share the same media drop and all be viewed simultaneously by the same microscope. The bottom surface of each micro-well has an optical quality finish. For example, FIG. 27A in U.S. Pat. No. 7,963,906 shows a drawing with dimensions for one exemplary embodiment. In this version, there are 25 micro-wells spaced closely together within a 1.7×1.7 mm field-of-view. FIG. 27B of U.S. Pat. No. 7,963,906 shows a 3D-view of the micro-wells, which are recessed approximately 100 microns into the dish surface. The petri dish may have 1 to 25 or more micro-wells. For example, in one embodiment, a petri dish with 12 wells is utilized. Fiducial markers, including letters, numbers, and other markings, are included on the dish to help with identification. All references cited herein are incorporated by reference in their entireties.

EXAMPLES

The following examples are put forth so as to provide those of ordinary skill in the art with a disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Quantitative Measurement of Blastocyst Expansion and Collapse Dynamics

Figure 2:
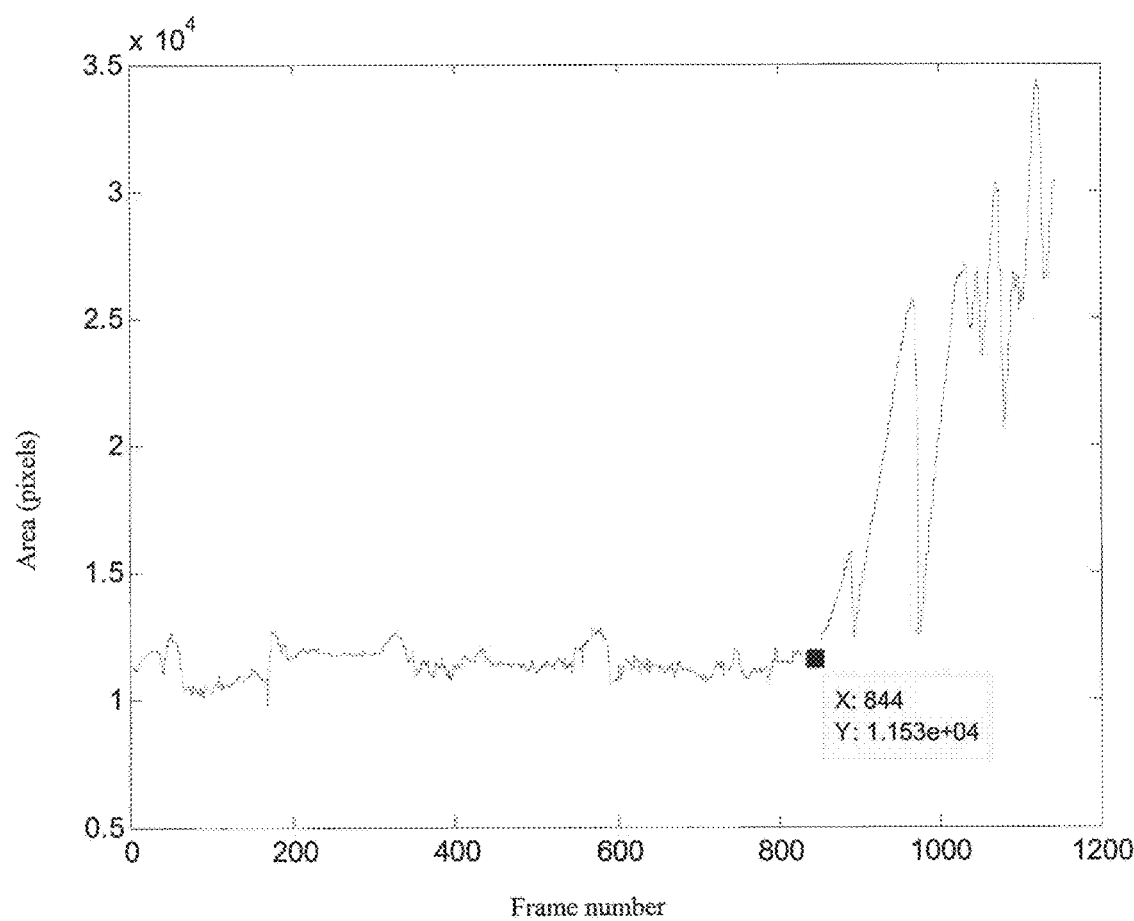
FIG. 2 is a line graph that shows the area of the embryo outer boundary segmentation vs. time, where increases in area over time indicate expansion and decreases in area over time indicate collapse.

In order to quantitatively measure blastocyst expansion and collapse dynamics, embryos were imaged using a time-lapse imaging system through day 5 at an image frequency of 5 minutes per frame. First, the embryo outer boundary segmentation was generated for every frame in a time lapse image sequence as illustrated in FIG. 1. The area of the embryo outer boundary segmentation was then calculated and plotted against time (FIG. 2). Timings, durations, and frequencies of blastocyst expansion and collapse were then analyzed. Increases in area over time indicate blastocyst expansion, and decreases in area over time indicate collapse. This data demonstrates that a single image feature, the area of the embryo outer boundary segmentation, can be used to identify the onset and resolution of expansion and collapse.

Example 2

Quantitative Measurement of Compaction and Cavitation Dynamics

Compaction and cavitation are gradual transitioning processes, and it is challenging for human observers to identify a single time point when a transition occurs. In order to quantitatively measure compaction and cavitation events, embryos were imaged using a time-lapse imaging system through day 5 at an image frequency of 5 minutes per frame.

Figure 3:
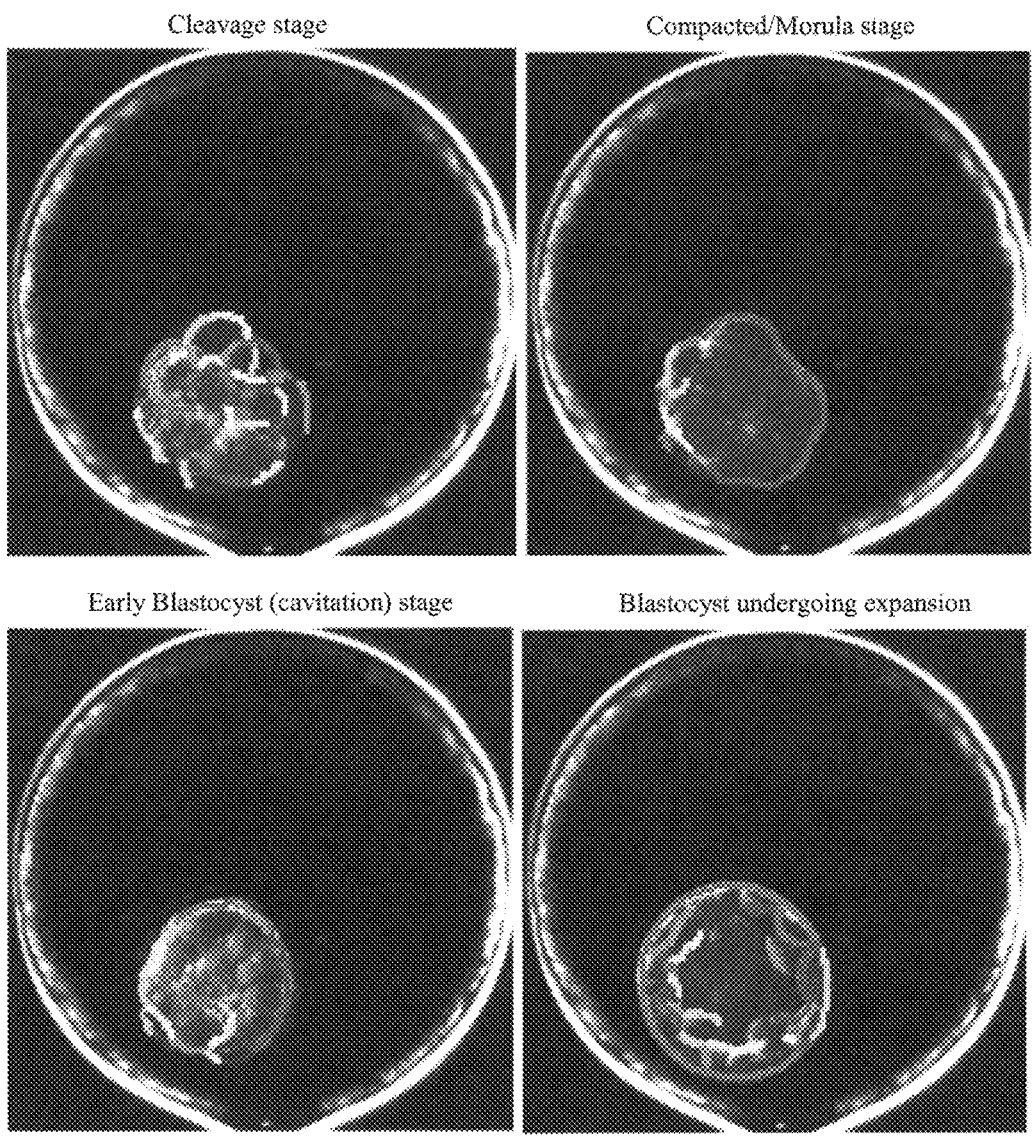
FIG. 3 is a series of time-lapse images that depicts embryo cell boundary segment distributions at the cleavage stage (top left), compacted/morula stage (top right), early blastocyst (cavitation) stage (bottom left), and blastocyst undergoing expansion (bottom right).
Figure 4:
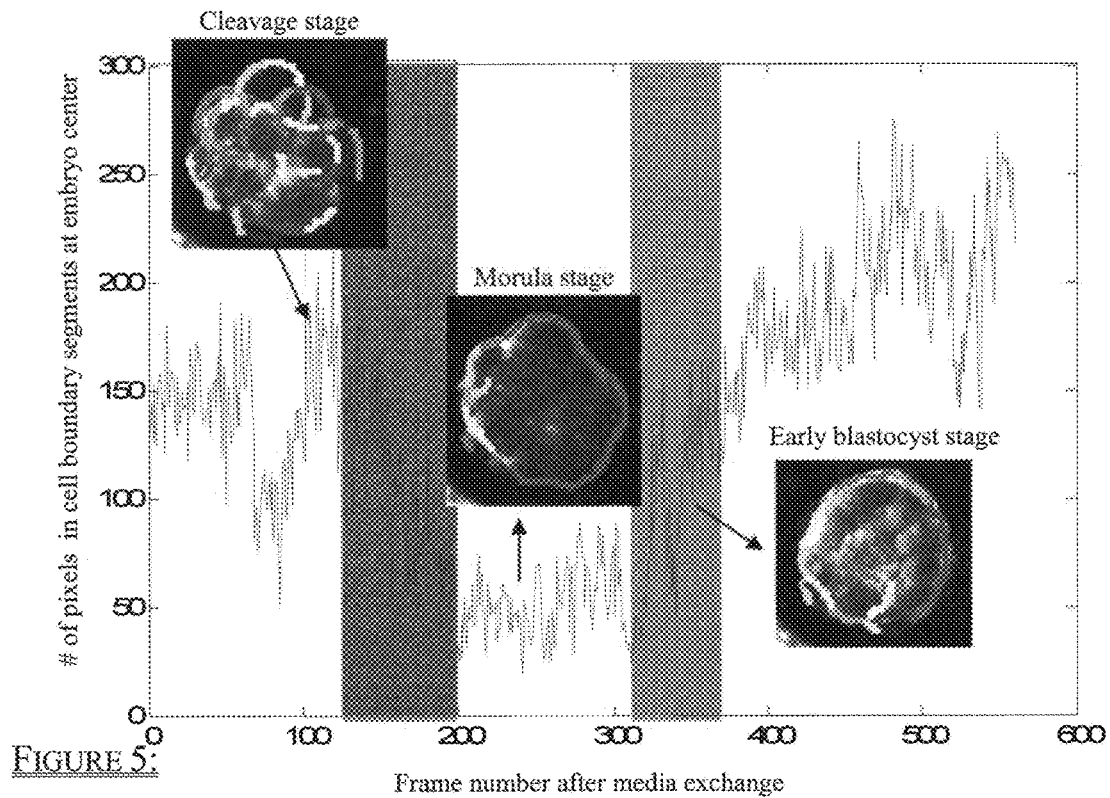
FIG. 4 is a line graph that shows the number of pixels in embryo cell boundary segments at the embryo center vs. time. Three example embryo images with labeled segments at cleavage, morula and early blastocyst (cavitation) are shown on top of the curve. The compaction process is highlighted in the first shaded box and corresponds to a decrease in number of pixels in segments, and the cavitation process is highlighted in the second shaded box and corresponds to an increase in number of pixels in segments.

First, analysis was performed on all images to obtain coherent boundary features (i.e., segments) as shown in FIG. 3. The compaction process correlates to a decrease in edge-based segments located in the center of the embryo, while the cavitation process correlates to an increase in edge-based segments located in the center of the embryo. Therefore, segment distribution pattern changes over time were analyzed, and an example is shown in FIG. 4.

Figure 5:
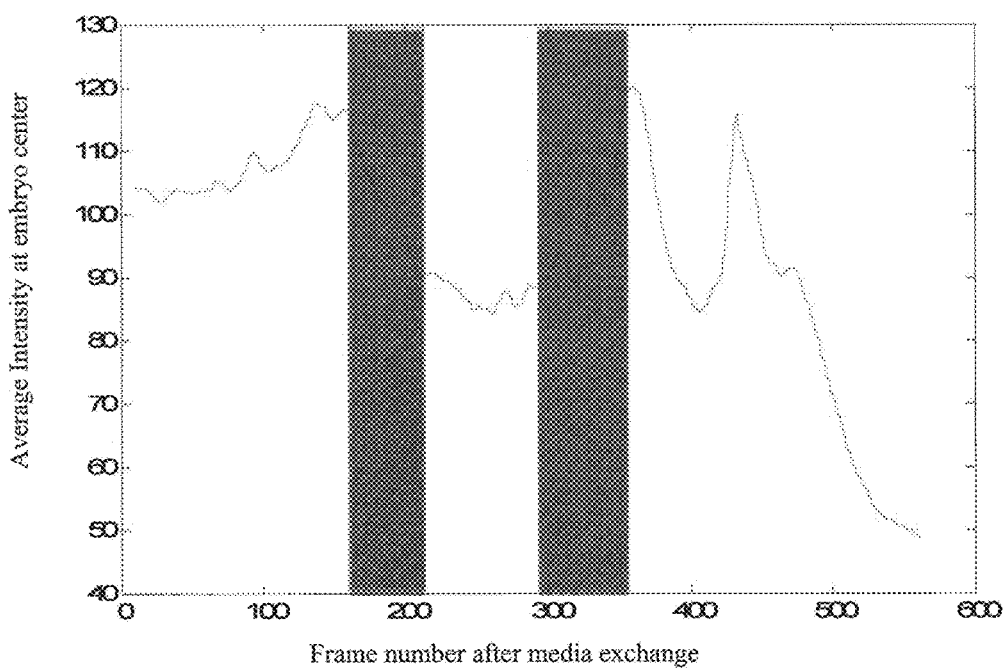
FIG. 5 is a line graph that shows average intensity at embryo center vs. time. The compaction process is highlighted in the first shaded box and corresponds to a decrease in average intensity, and the cavitation process is highlighted in the second shaded box and corresponds to an increase in average intensity.

The second image feature analyzed was the average of integrated image intensity changes at the center of the embryo over time. The compaction process correlates to a decrease in intensity at the center of the embryo, while the cavitation process correlates to an increase in intensity at the center of the embryo. Therefore, intensity changes at the center of the embryo over time were analyzed, and an example is shown in FIG. 5.

Figure 6:
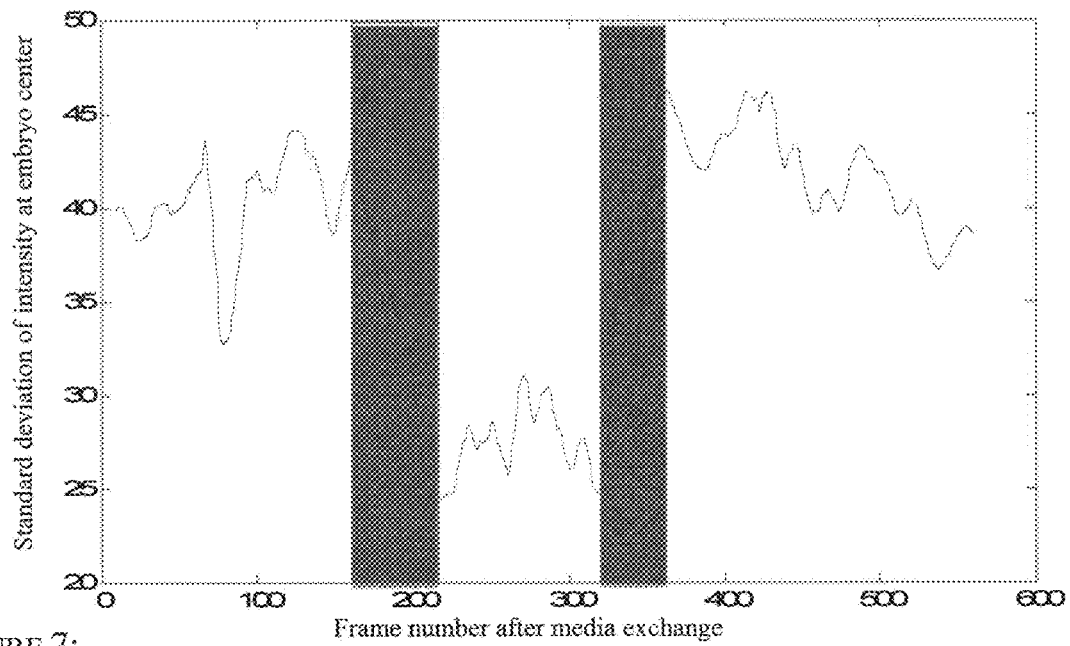
FIG. 6 is a line graph that shows standard deviation of intensity at embryo center vs. time. The compaction process is highlighted in the first shaded box and corresponds to a decrease in standard deviation of intensity, and the cavitation process is highlighted in the second shaded box and corresponds to an increase in standard deviation of intensity.

The third image feature analyzed was the standard deviation of image intensities at the center of the embryo over time. The compaction process correlates to a decrease in standard deviation of intensity at the center of the embryo, while the cavitation process correlates to an increase in standard deviation at the center of the embryo. Therefore, changes in standard deviation of intensity at the center of the embryo were analyzed, and an example is shown in FIG. 6.

In addition to the three image features described above, several other changes in image features over time that are markers of compaction and cavitation were also analyzed. The additional image features include shape of the embryo, the texture features at the edge or center of the embryo, scale-invariant feature transform (SIFT), and features generated by Speeded Up Robust Features (SURF).

This data demonstrates that three image features (distribution of edge-based segments, image intensity changes at the center of the embryo, and changes in standard deviation of image intensity at the center of the embryo) can be used alone or in combination to identify the onset and resolution of compaction and cavitation.

Figure 7:
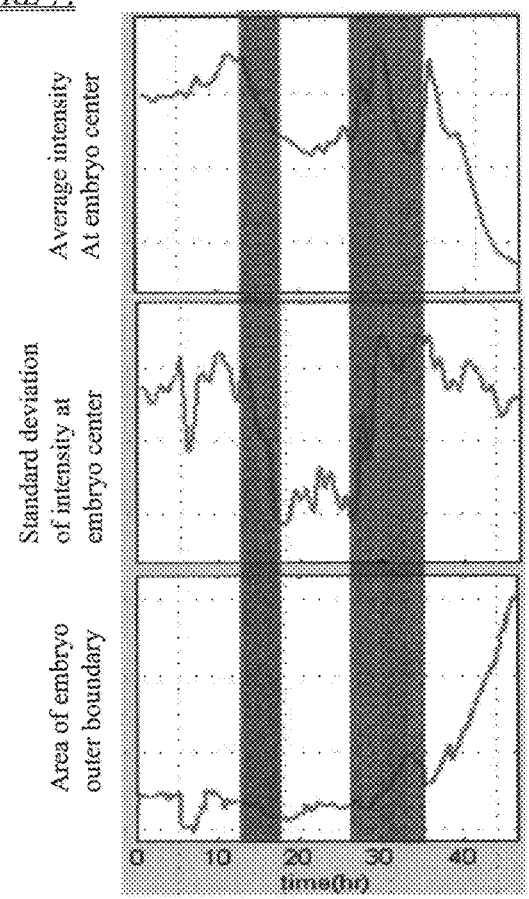
FIG. 7 is a series of line graphs that show multiple image features (i.e., area of the embryo outer boundary segmentation (bottom), standard deviation of intensity at embryo center (middle), and average intensity at embryo center (top)) vs. time used to extract timing measurements for compaction (first box), cavitation (second box), blastocyst expansion (third box) and blastocyst collapse (fourth box).

Furthermore, the data from Example 1 can be combined with the data related to detecting compaction and cavitation in order to establish robust definitions and measurements of compaction, cavitation and blastocyst expansion and collapse. As shown in FIG. 7, the data can be combined to robustly identify the distinct start and stop (i.e., onset and resolution) of each of the compaction, cavitation, expansion and collapse parameters. Therefore, these parameters can be accurately and efficiently be measured automatically or semi-automatically with manual inputs.

Example 3

Cavitation Parameters are Predictive of Aneuploidy and can be Combined with Other Parameters to Classify Risk of Embryonic Aneuploidy It has been reported that more than 50% of the human embryos cultured in IVF clinics are aneuploid embryos that have an abnormal number of chromosomes. These aneuploid embryos have lower implantation rates and are not likely to result in live birth of healthy babies. Currently, pre-implantation genetic screening (PGS) is the most effective approach to select against aneuploidy embryos. However, due to its high cost, labor intensive requirements and invasive nature, less than 10% of patients that are treated for assisted reproduction undergo PGS prior to embryo transfer.

In order to develop a non-invasive time-lapse enabled assay to assess the risk of embryos being aneuploid, it was discovered that by assessing the tCav parameter, alone or in combination with other cellular parameters, embryo morphology and patient information, the likelihood of an embryo being aneuploid can be determined.

Figure 9:
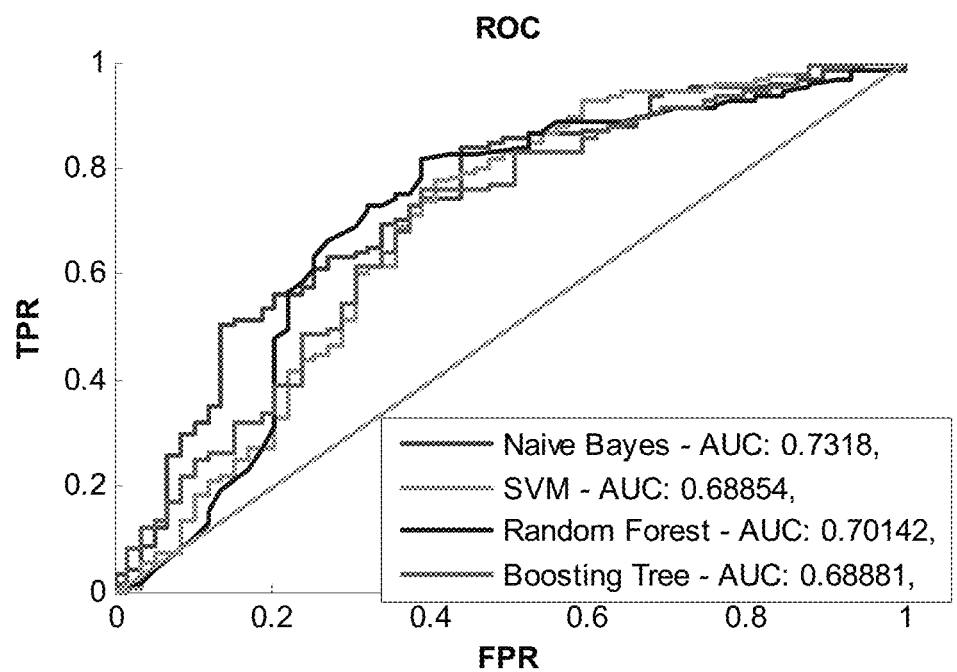
FIG. 9 shows by the use of four different classifiers that embryo age combined with the number of 2PN embryos, time to cavitation and Psyn is predictive of aneuploidy in human embryos.

By evaluating tCav values from time-lapse data of 376 embryos, it was discovered that euploid embryos have shorter tCav than aneuploid embryos. As shown in FIG. 8, the tCav parameter has a statistically significant different distribution (p=0.0002, Wilcoxon-Mann-Whitney test) between aneuploid embryos (74.4±6.2 hours, n=128) and euploid embryos (72.3±5.7 hours, n=278).

tCav is combined with age, #2PN, and Psyn to predict aneuploidy. Four classifiers (Naïve Baysian, SVM, Random Forest, and Boosting Tree) were trained based on 276 embryos, and AUC values were evaluated for a different set of 184 embryos. Receiver Operating Characteristic (ROC) curves from these four classifiers were shown in FIG. 9. An AUC of 0.73 was achieved. These data show that tCav together with other parameters can be used to provide a probability estimate for embryo aneuploidy.

Example 4

Expansion Parameters are Predictive of Aneuploidy and can be Combined with Other Parameters to Classify Risk of Embryonic Aneuploidy In order to develop a non-invasive time-lapse enabled assay to assess the risk of embryos being aneuploid, it was discovered that by assessing the Pexp-area parameter, alone or in combination with other cellular parameters, embryo morphology and patient information, the likelihood of an embryo being aneuploid can be determined.

Figure 10:
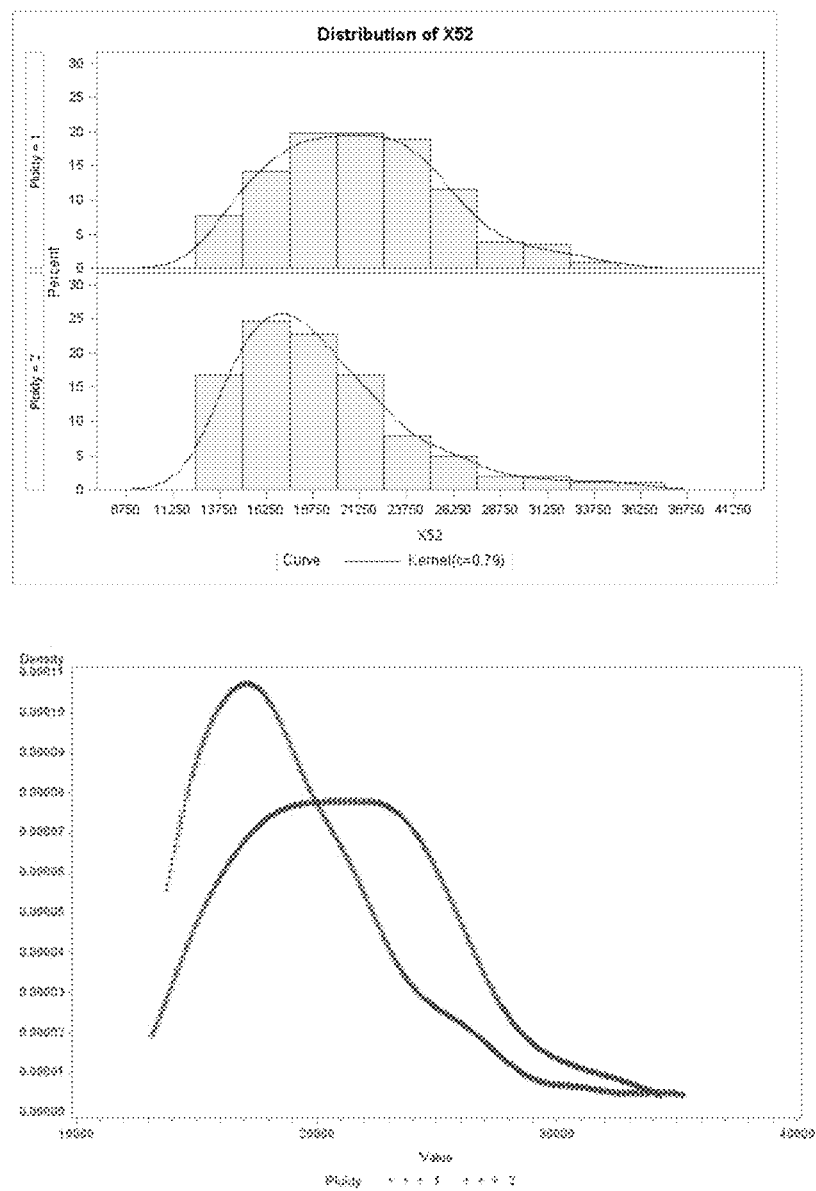
FIG. 10 shows that the average size after initial expansion is predictive of aneuploidy in human embryos

By evaluating Pexp-area values from time-lapse data of 374 embryos, it was discovered that euploid embryos have larger Pexp-area than aneuploid embryos. As shown in FIG. 10, the Pexp-area parameter has a statistically significant different distribution (p<0.0001, Wilcoxon-Mann-Whitney test) between euploid embryos (21±4 k pixels, n=258) and aneuploid embryos (18±4 k pixels, n=116).

tCav is combined with age and P3 to predict aneuploidy. Four classifiers (Naïve Baysian, SVM, Random Forest, and Boosting Tree) were trained based on 224 embryos, and AUC values were evaluated for a different set of 150 embryos. Receiver Operating Characteristic (ROC) curves from these four classifiers were shown in FIG. 11. An AUC of 0.74 was achieved. Based on the classifier output, the training dataset was divided into five categories containing similar numbers of embryos, and the threshold values determined in the training dataset was applied to an indepedent test dataset. The % euploid embryos in each category 1 through 5 are shown in FIG. 11, where the top category had >90% euploid embryos and the bottom category had 40-50% euploid embryos. These data show that Pexp-area together with other parameters can be used to provide a probability estimate for embryo aneuploidy.

Example 5

Expansion Parameters are Predictive of Implantation Potential for Euploid Embryos Aneuploid embryos have lower implantation rates and are not likely to result in live birth of healthy babies, and hence selecting euploid embryos for transfer by PGS is a strategy for improving embryo selection. However, not all euploid embryos implant and result in live birth. Therefore, PGS patients who have multiple euploid embryos available for transfer are in need of tools that predict implantation potential to further aid selection among euploid embryos.

In order to develop a non-invasive time-lapse enabled assay to assess the implantation potential of euploid embryos, it was discovered that by assessing expansion parameters (Exp Time, Avg Exp Time), alone or in combination with other cellular parameter(s), embryo morphology and patient information, the likelihood of implantation for an euploid embryo can be determined.

Figure 15:
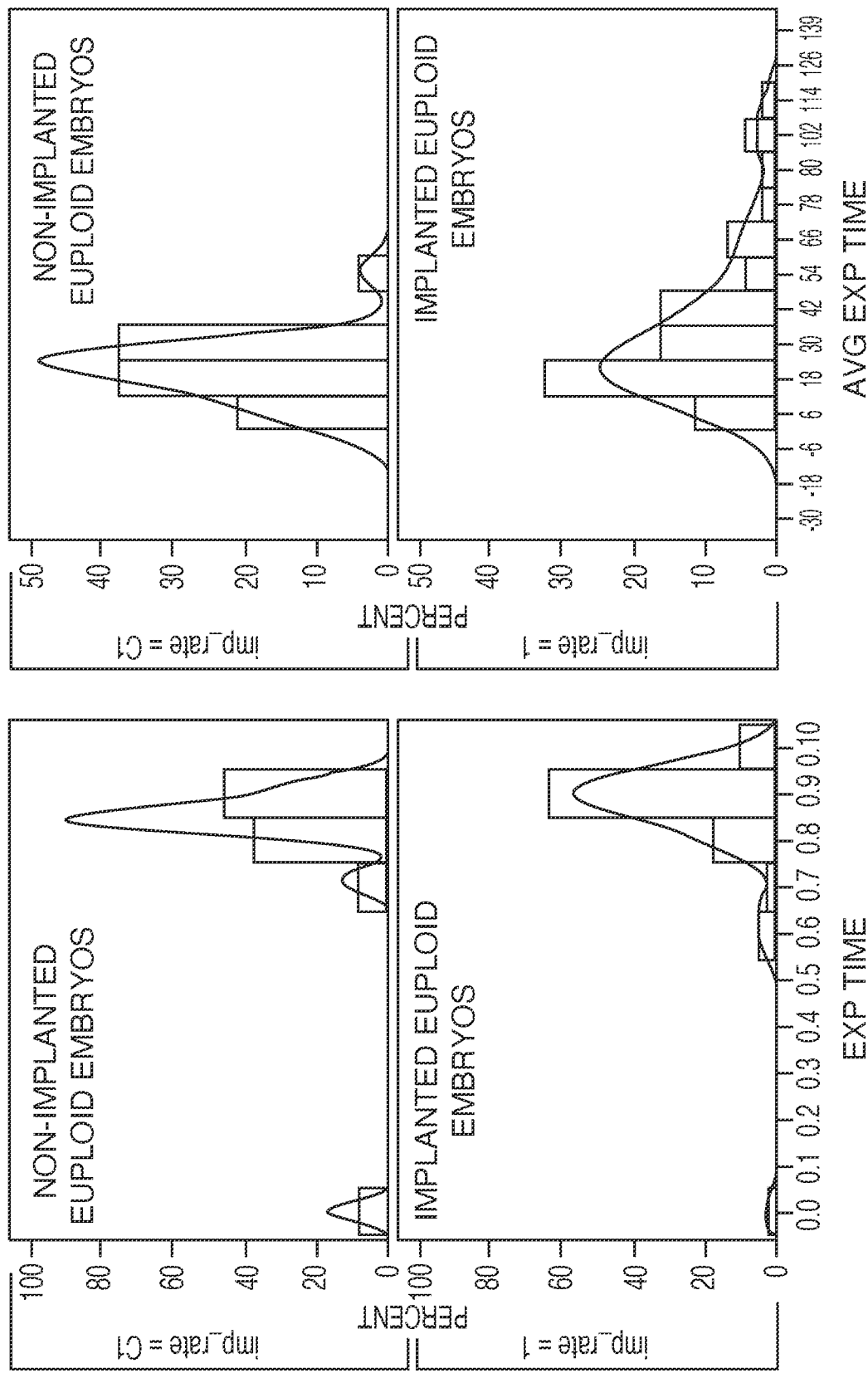
FIG. 15 shows that the percentage of time spent in expansion (Exp Time) and the average time spent in each expansion event (Avg Exp Time) is predictive of the likelihood that euploid embryos will implant into the uterus.

By evaluating Exp Time values from time-lapse data of 67 transferred euploid embryos, it was discovered that implanted euploid embryos spent longer time in expansion than non-implanted euploid embryos. As shown in FIG. 15, the Exp Time parameter has a statistically significant different distribution (p=0.01, Wilcoxon-Mann-Whitney test) between implanted euploid embryos (89%±16%, n=43) and non-implanted euploid embryos (85%±24%, n=24).

By evaluating Avg Exp Time values from time-lapse data of 67 transferred euploid embryos, it was discovered that implanted euploid embryos had longer continuous expansion per event than non-implanted euploid embryos. As shown in FIG. 15, the Avg Exp Time parameter has a statistically significant different distribution (p=0.03, Wilcoxon-Mann-Whitney test) between implanted euploid embryos (27±27, n=43) and non-implanted euploid embryos (23±12, n=24). These numbers represent the number of frames with each frame being 5 minutes long. Thus, calculated in minutes, the average amount of time implanted euploid embryos spend in each expansion event is (135 minutes±135 minutes) while the average amount of time a non-implanted euploid embryo spends in each expansion event is (115 minutes±60 minutes).

These data show that Exp Time and/or Avg Exp Time can be used to provide a probability estimate for euploid embryo implantation. A longer Exp Time and/or Avg Exp Time can be used to select euploid embryos that are more likely to implant, whereas a shorter Exp Time and/or Avg Exp Time can be used to deselect euploid embryos that are less likely to implant. Thus, Exp Time and/or Avg Exp Time may be used alone, or in combination with previously described parameters to select among euploid embryos.

The invention claimed is:
1. A method for treating infertility, comprising:
 a) providing a computer system comprising:
  i) a time-lapse microscope comprising a camera and software for automatically acquiring a series of time-sequential images of one or more human embryos contained in a multi-well culture dish comprising a plurality of microwells with a camera of at least one time-lapse microscope, wherein said one or more human embryos are between about three (3)-five (5) days following fertilization; and ii) a computer in communication with said microscope, said computer comprising image analysis software;

b) extracting one or more image features from said series of time-sequential images with said image analysis software, wherein said one or more image features comprise a plurality of cell parameters wherein at least one of said plurality of cell parameters is selected from the group consisting of a time from first cleavage to cavitation (tCav) parameter and an average size after initial expansion (Pexp-area) parameter;

c) classifying said one or more human embryos as: i) euploid when said Pexp-area parameter is within 21.25-20.75 k pixels or when said tCav parameter is within 72.65-71.95 hours; or ii) aneuploid when said Pexp-area parameter is within 19.67-16.33 k pixels or when said tCav parameter is within 74.97-73.83 hours;

d) selecting a euploid human embryo based on said classifying; and e) treating a recipient with in vitro fertilization by single embryo transfer of said selected human embryo.

2. The method of claim 1 wherein said image features include at least one of: cell boundary segment distribution, average intensity at embryo center, or standard deviation of intensity at embryo center.

3. The method of claim 1 further comprising determining a parameter from said image features, wherein said parameter identifies one of:

duration of expansion, duration of collapse, frequency of collapse, degree of expansion, degree of collapse, rate of expansion, rate of collapse, average embryo size after initial expansion and the time interval between expansion and collapse.

4. The method of claim 1 wherein said one or more human embryos have not been frozen.

5. The method of claim 1 wherein said one or more human embryos have been frozen.

6. The method of claim 1, wherein said image feature is selected from the group consisting of embryo shape, texture in the region defined around the embryo edge, and texture at embryo center.

7. The method of claim 6, wherein said extracting of said image features is selected from the group consisting of a shape based method, a low level method, a curvature based method and a combination thereof.

8. The method of claim 7, wherein said shape based method is at least one of template matching, Hough transforms or a combination thereof.

9. The method of claim 1, wherein said classifying uses a classifier selected from the group consisting of a nave Bayesian classifier, a SVM classifier, a Random Forest classifier and a Boosting Tree classifier.

10. The method of claim 1, wherein said selected human embryo is euploid and viable.

11. The method of claim 1, wherein said selecting comprises physically moving said selected human embryo from one location to another.

* * * * *